(12) United States Patent
McLaren

(10) Patent No.: US 11,638,800 B2
(45) Date of Patent: May 2, 2023

(54) HEADGEAR ADJUSTMENT MECHANISM

(71) Applicant: Fisher & Paykel Healthcare Limited, Auckland (NZ)

(72) Inventor: Mark Arvind McLaren, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1295 days.

(21) Appl. No.: 15/749,453

(22) PCT Filed: Aug. 12, 2016

(86) PCT No.: PCT/NZ2016/050128
§ 371 (c)(1),
(2) Date: Jan. 31, 2018

(87) PCT Pub. No.: WO2017/030447
PCT Pub. Date: Feb. 23, 2017

(65) Prior Publication Data
US 2018/0214656 A1    Aug. 2, 2018

Related U.S. Application Data

(60) Provisional application No. 62/205,275, filed on Aug. 14, 2015, provisional application No. 62/261,715, filed on Dec. 1, 2015.

(51) Int. Cl.
*A61M 16/06* (2006.01)
*A61M 16/16* (2006.01)
(Continued)

(52) U.S. Cl.
CPC .... *A61M 16/0683* (2013.01); *A61M 16/0069* (2014.02); *A61M 16/06* (2013.01);
(Continued)

(58) Field of Classification Search
CPC .......... A61M 16/0683; A61M 16/0069; A61M 16/109; A61M 16/06; A61M 16/16; A61M 2210/0618; A62B 18/084
See application file for complete search history.

(56) References Cited

U.S. PATENT DOCUMENTS 6,219,889 B1 * 4/2001 Lovato ................... A44B 11/12
24/170
2007/0130663 A1 * 6/2007 Lang ................. A61M 16/0633
2/9
(Continued)

FOREIGN PATENT DOCUMENTS

EP    1074195    6/2010
FR    2937255    4/2010
(Continued)

OTHER PUBLICATIONS

PCT International Search Report, PCT/NZ2016/050128, dated Nov. 28, 2016, in 5 pages.

*Primary Examiner* — Timothy A Stanis
(74) *Attorney, Agent, or Firm* — Knobbe, Martens, Olson & Bear, LLP

(57) ABSTRACT

A headgear assembly for retaining a respiratory mask on a user's face is provided. The headgear assembly comprising an adjustment mechanism or arrangement that includes a pair of rails configured to allow a first and second strap to be slideably moved relative to each other to adjust the size of the headgear assembly.

16 Claims, 43 Drawing Sheets

(51) Int. Cl.
*A61M 16/00* (2006.01)
*A61M 16/10* (2006.01)
*A62B 18/08* (2006.01)

(52) U.S. Cl.
CPC .......... *A61M 16/109* (2014.02); *A61M 16/16* (2013.01); *A61M 2210/0618* (2013.01); *A62B 18/084* (2013.01)

(56) References Cited

U.S. PATENT DOCUMENTS

2007/0245467 A1* 10/2007 Lilenthal .................. A42B 3/14
2/416
2011/0047674 A1* 3/2011 Sheppard ................. A42B 1/22
2/195.2
2013/0220327 A1* 8/2013 Barlow ............. A61M 16/0605
128/205.25
2014/0216476 A1 8/2014 Brace et al.

FOREIGN PATENT DOCUMENTS

GB 2145767 4/1985
WO WO-2014025267 A1 * 2/2014 ............ A61M 16/06

* cited by examiner

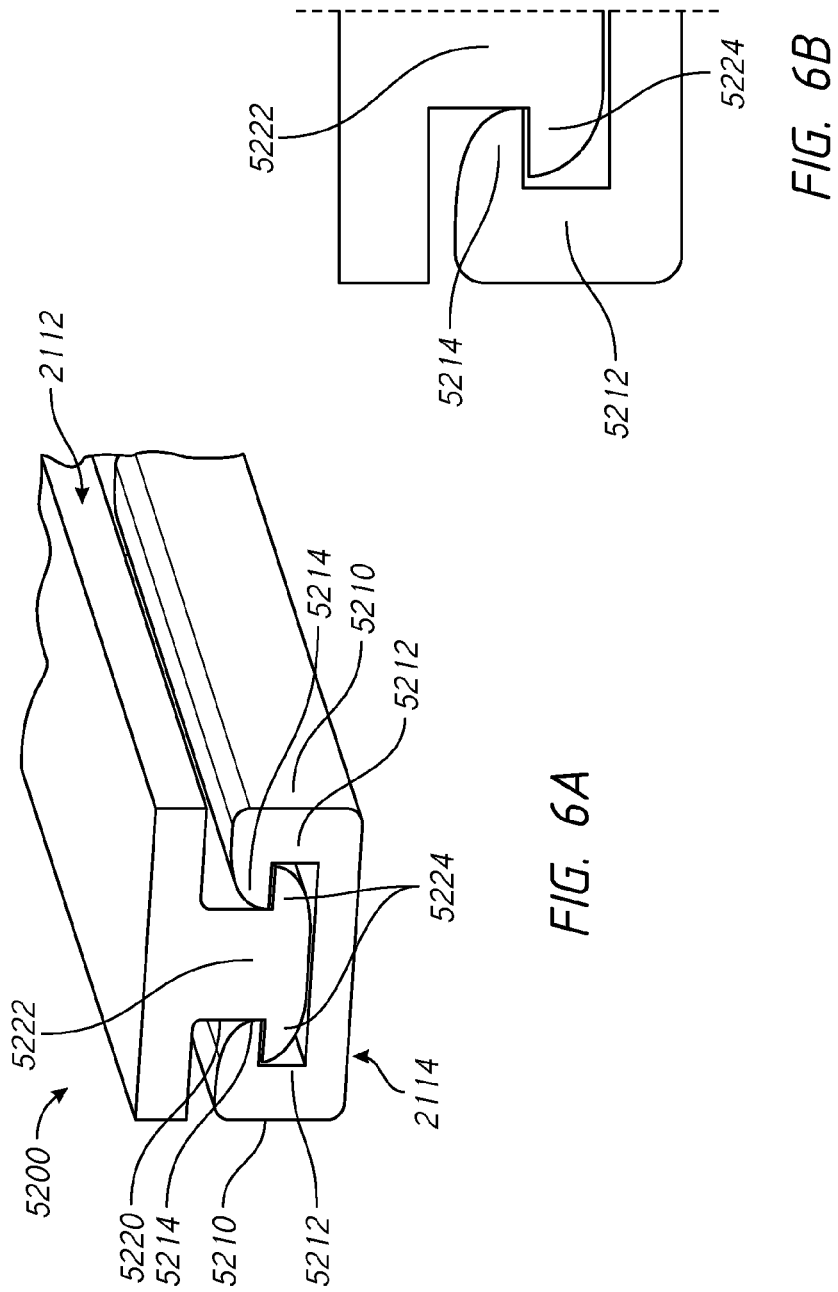

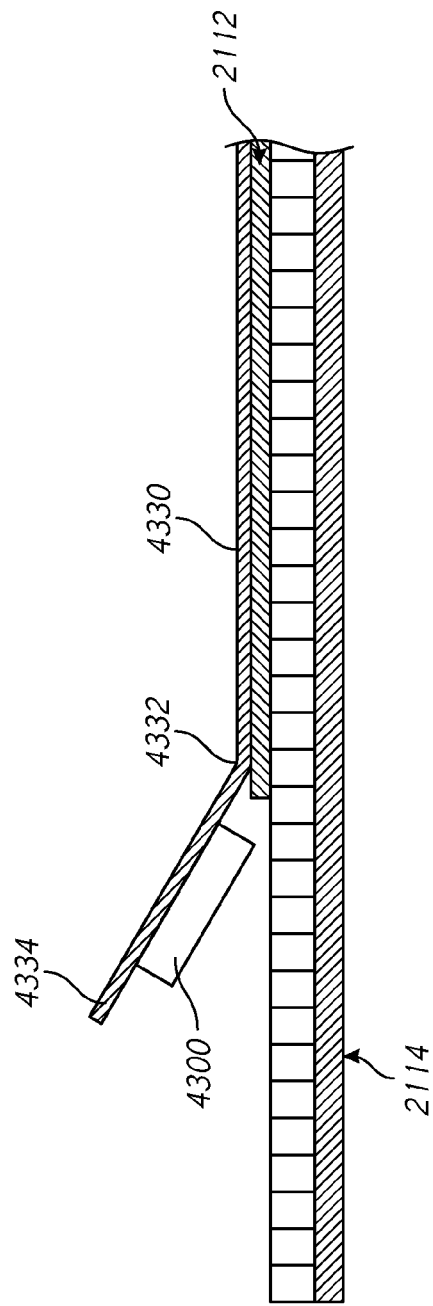

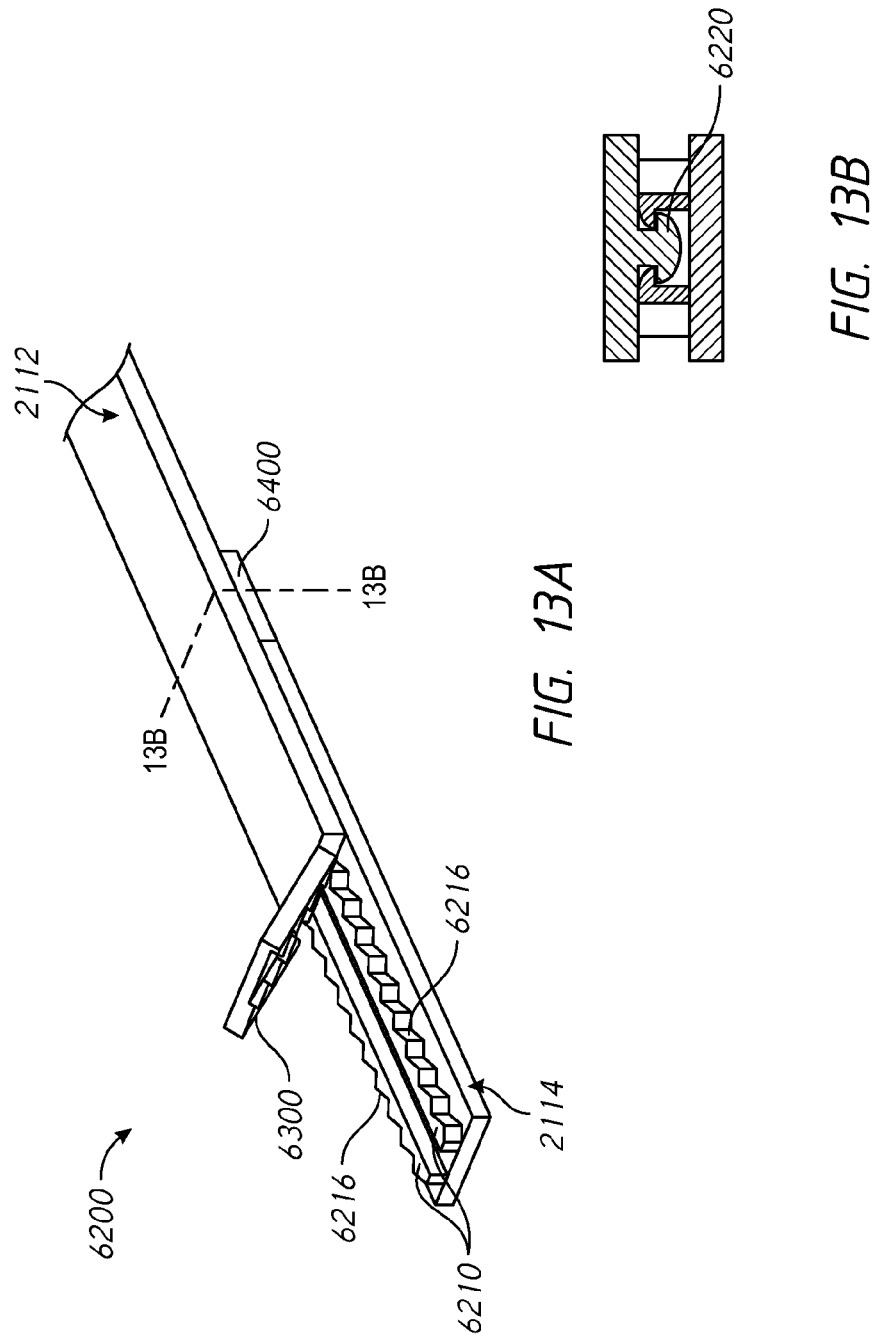

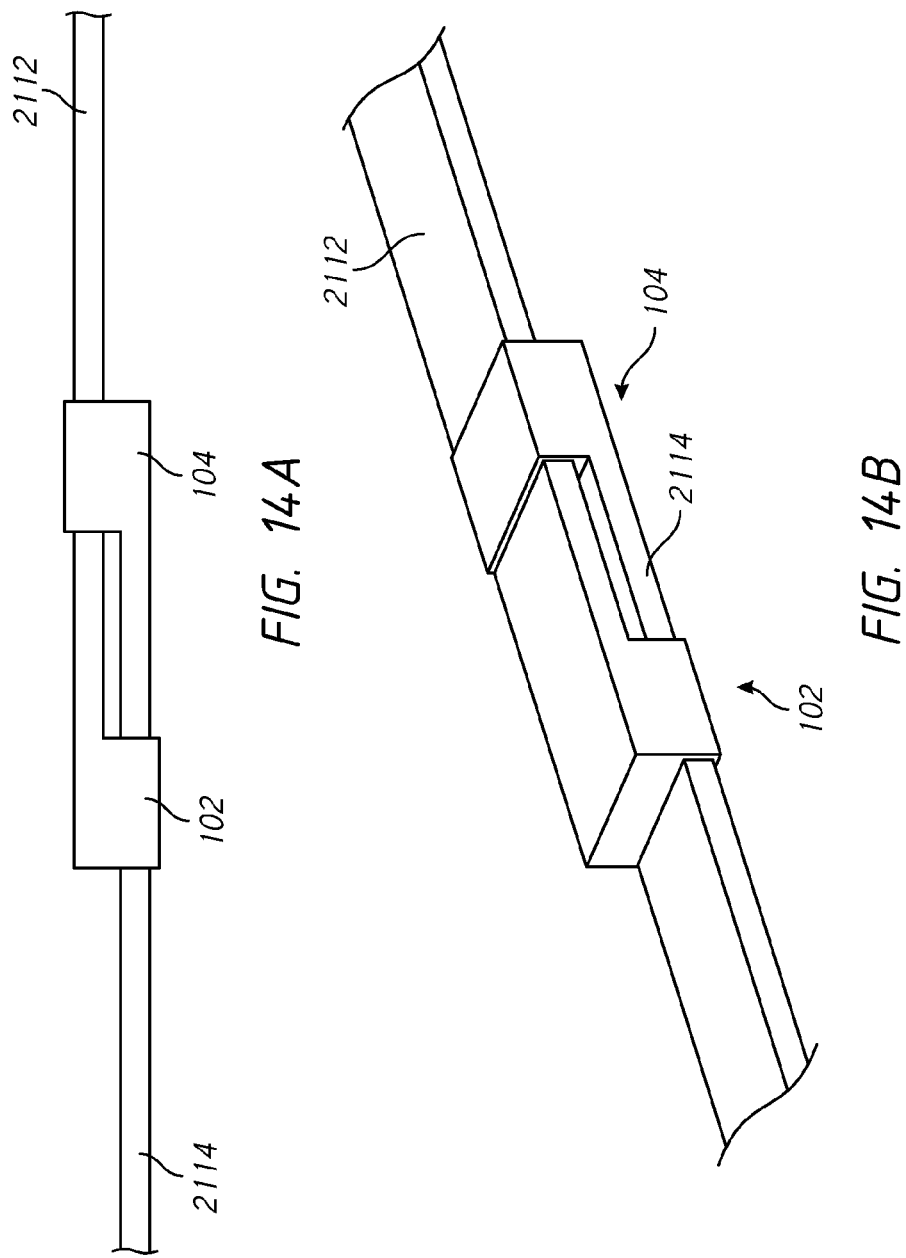

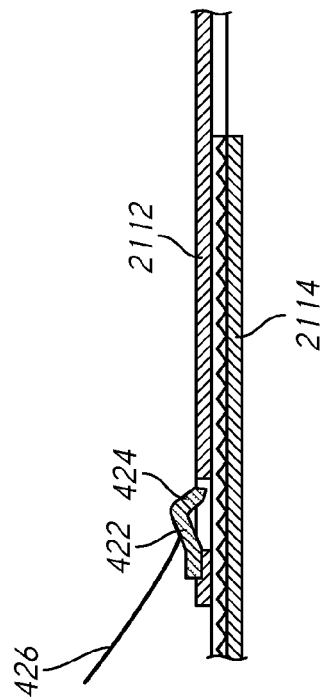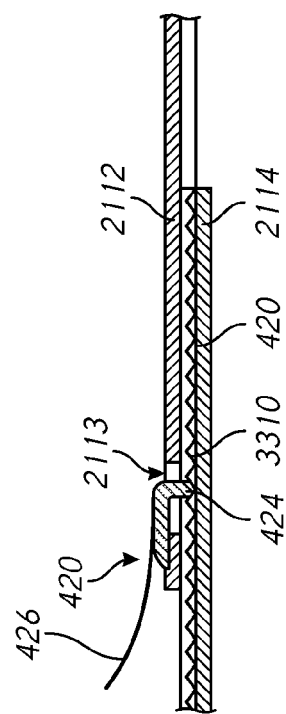

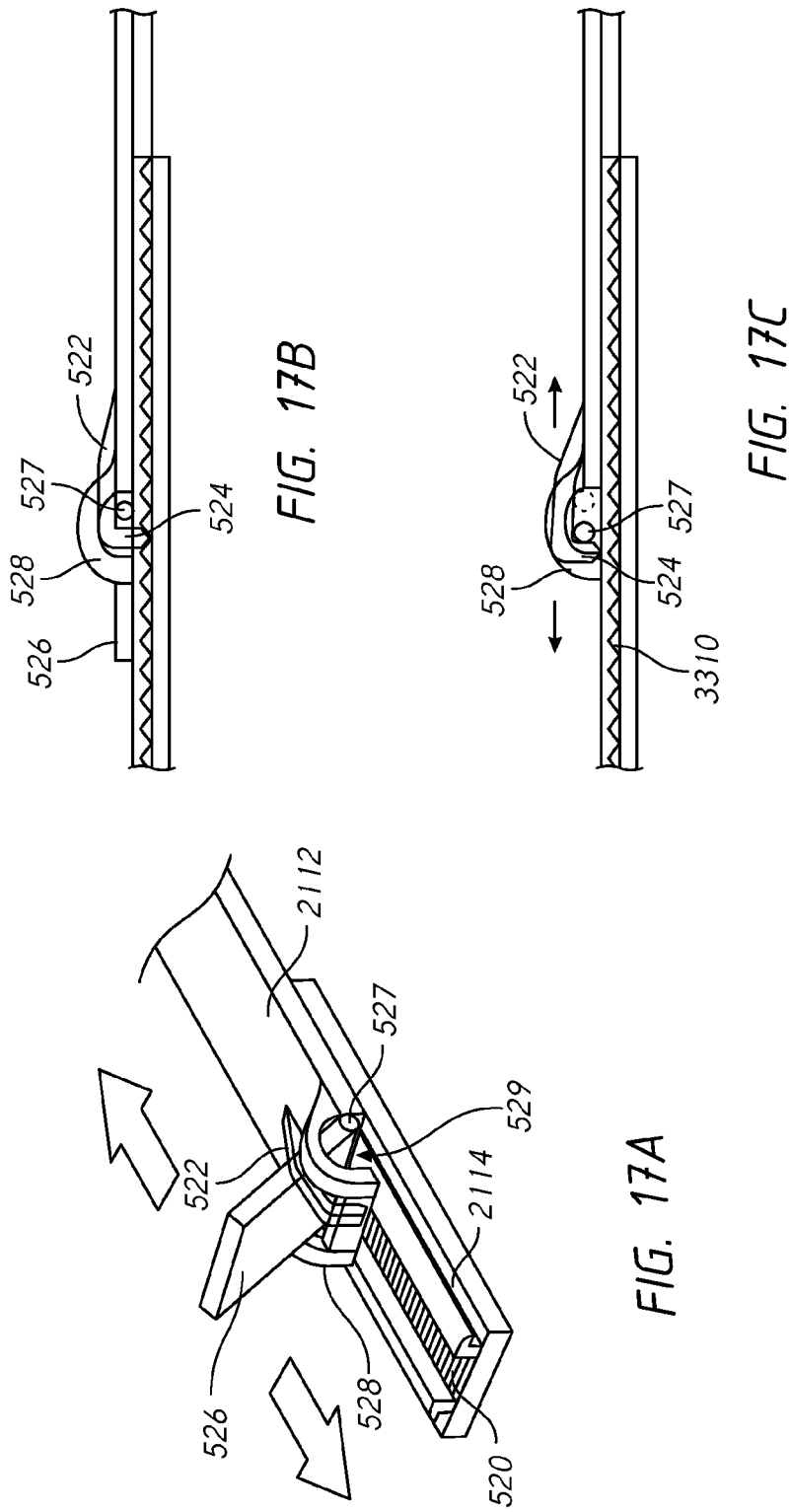

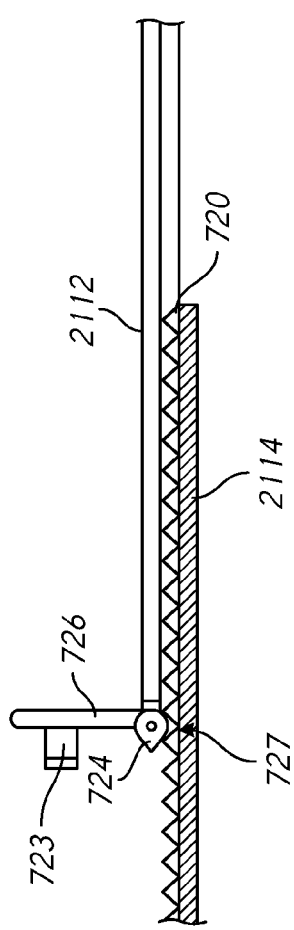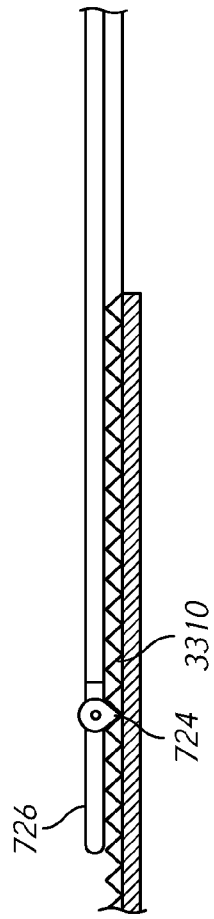

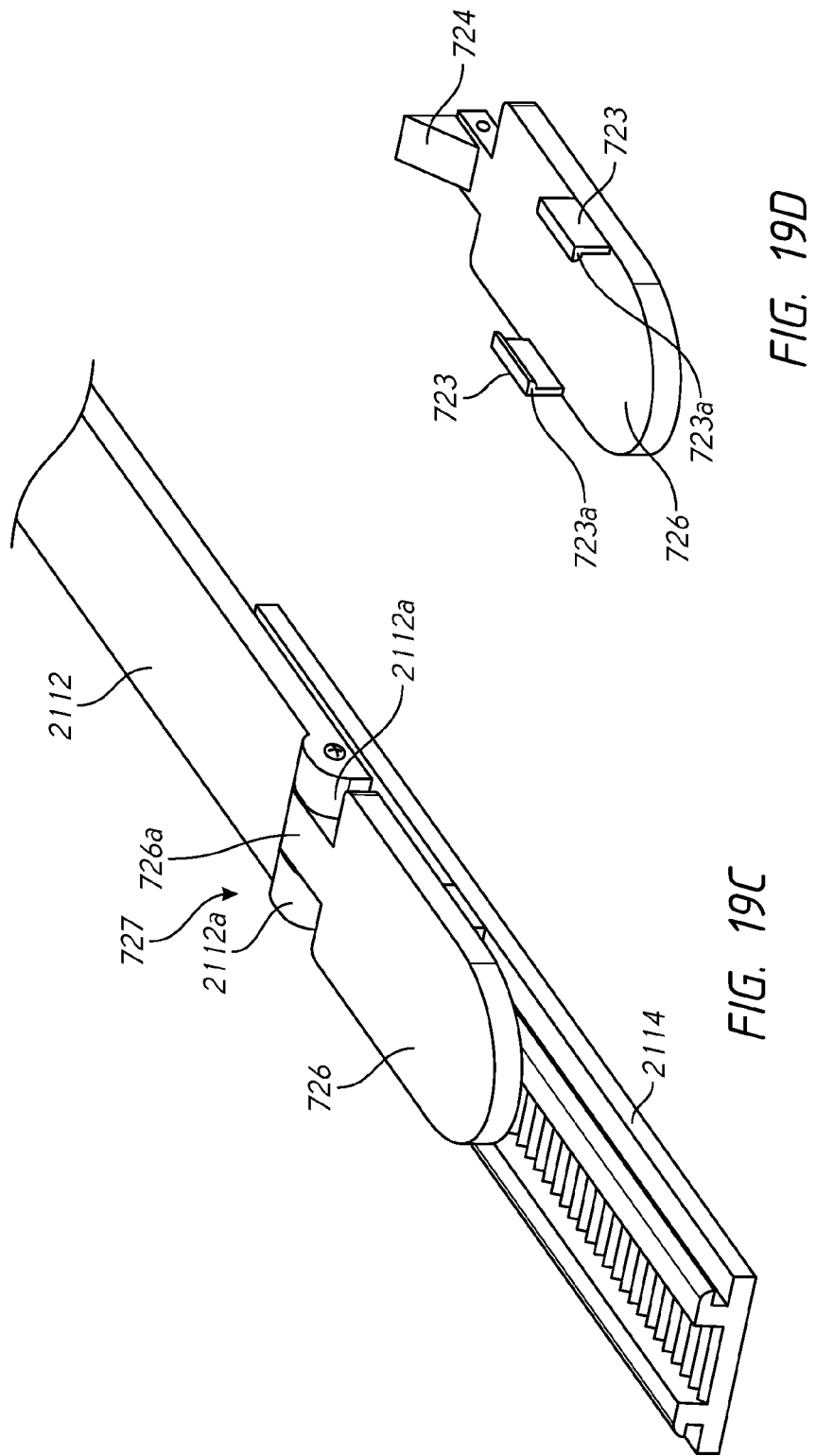

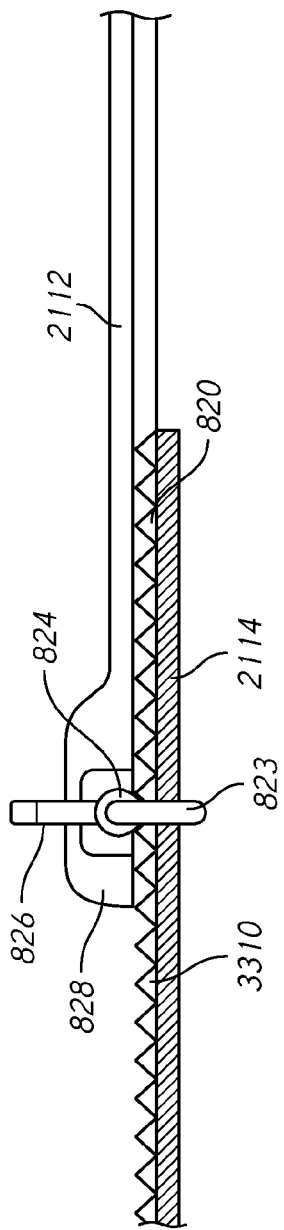
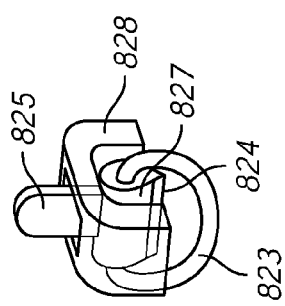
FIG. 20A
FIG. 20B

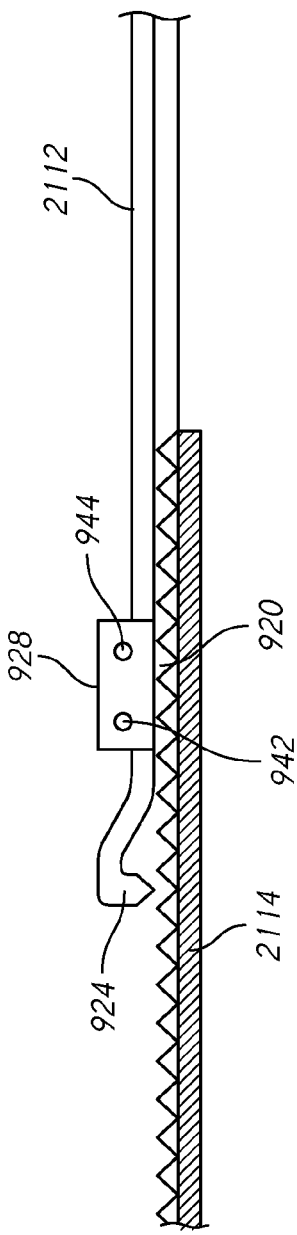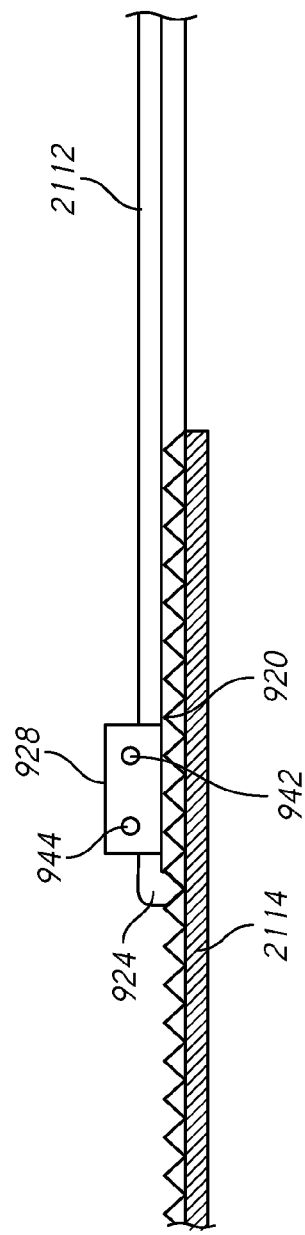

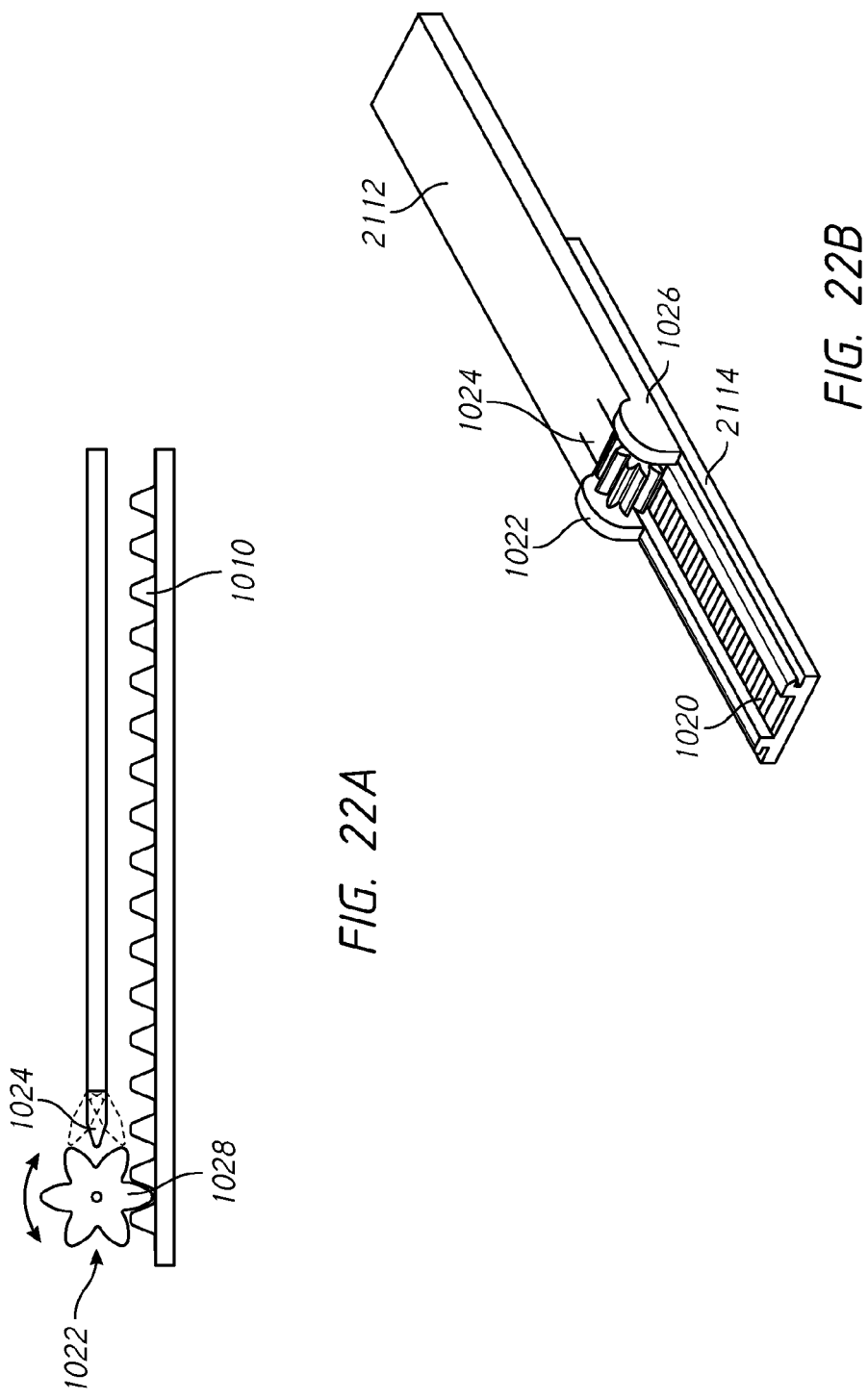

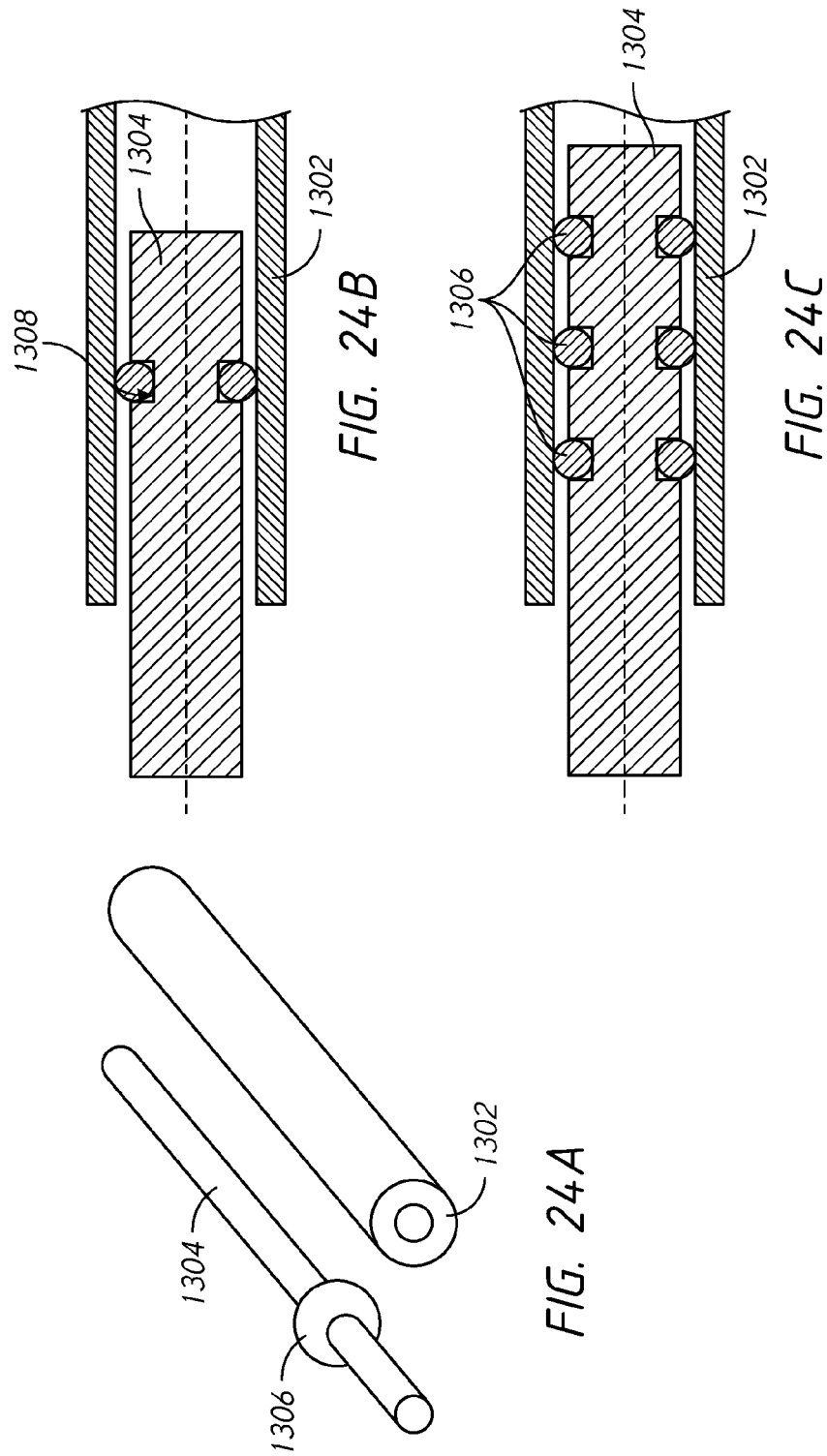

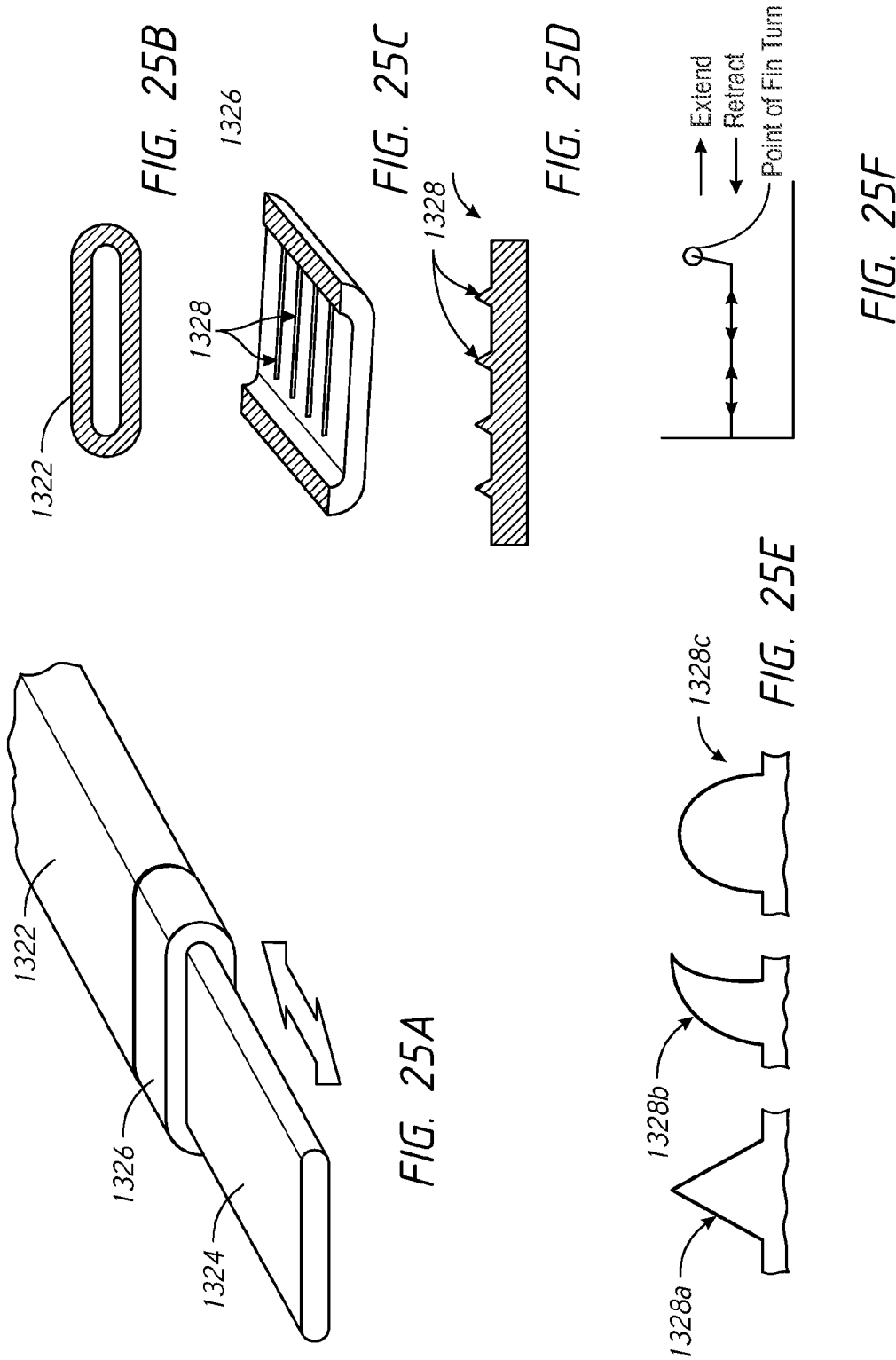

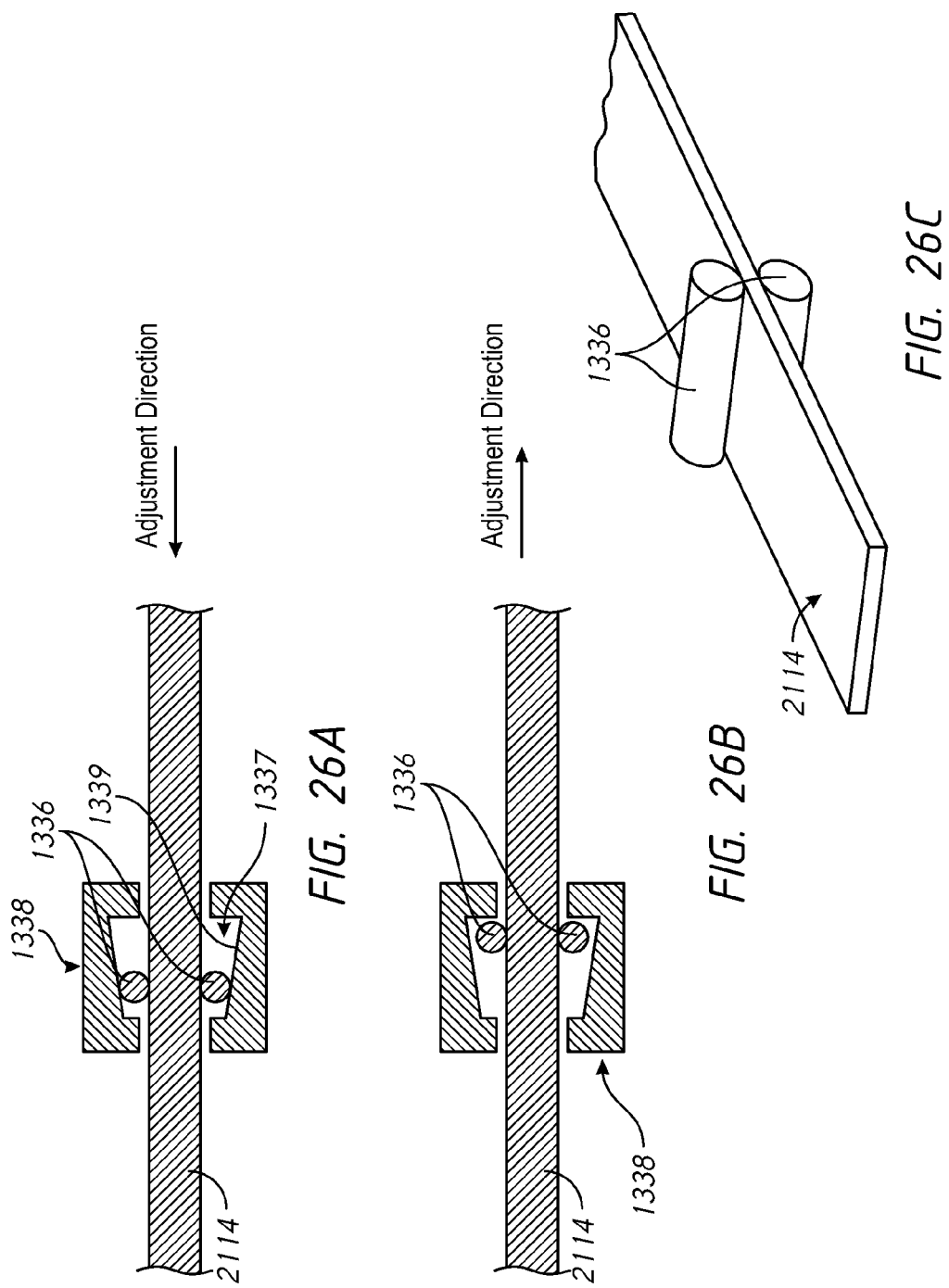

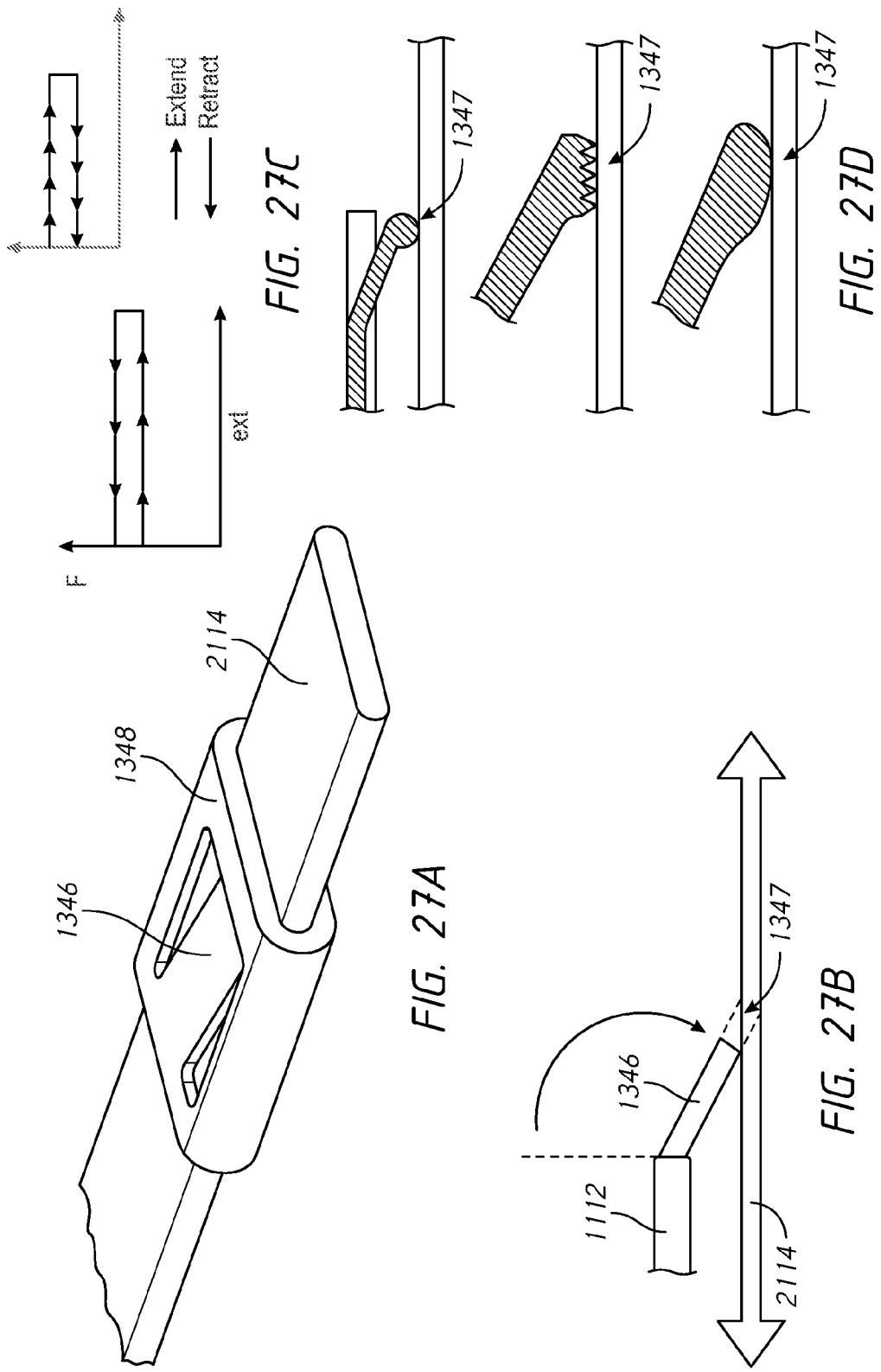

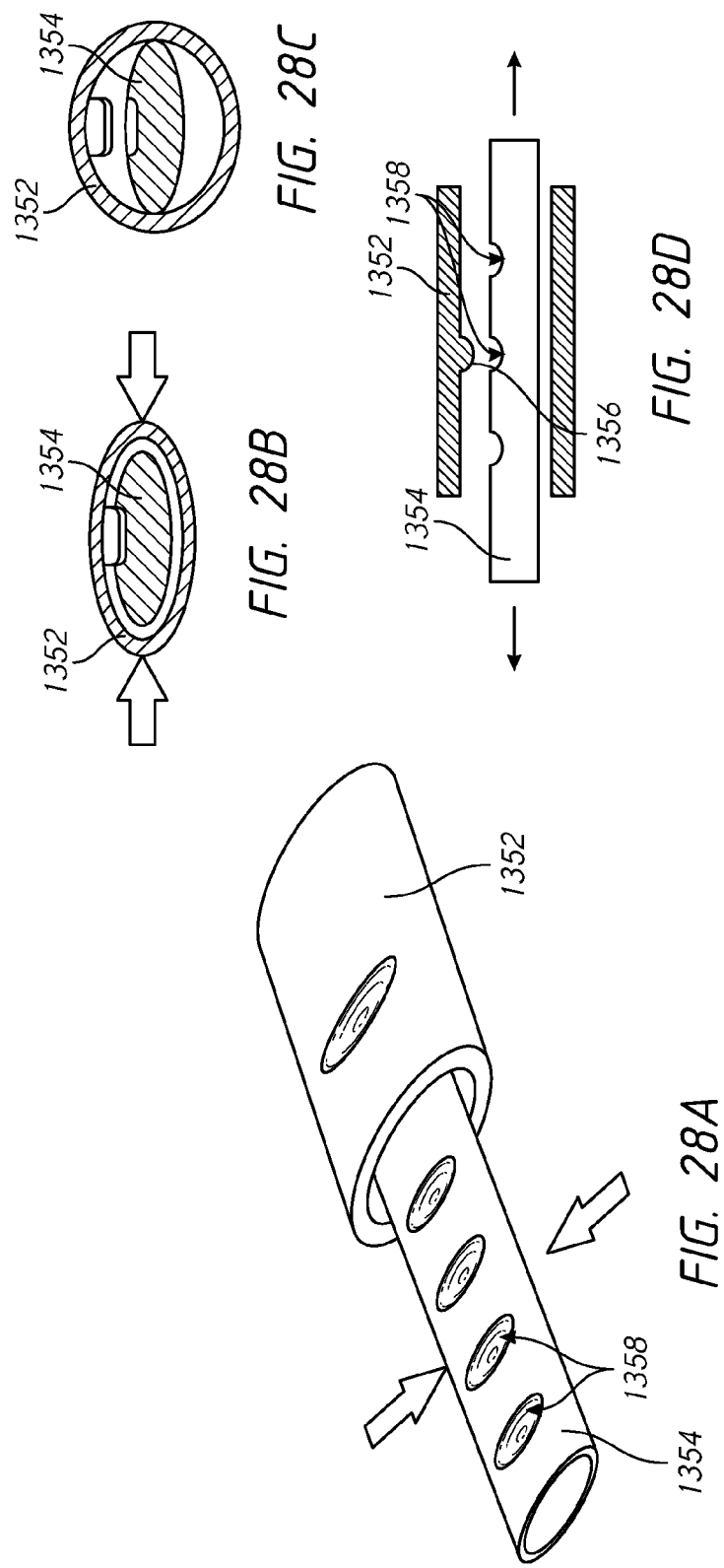

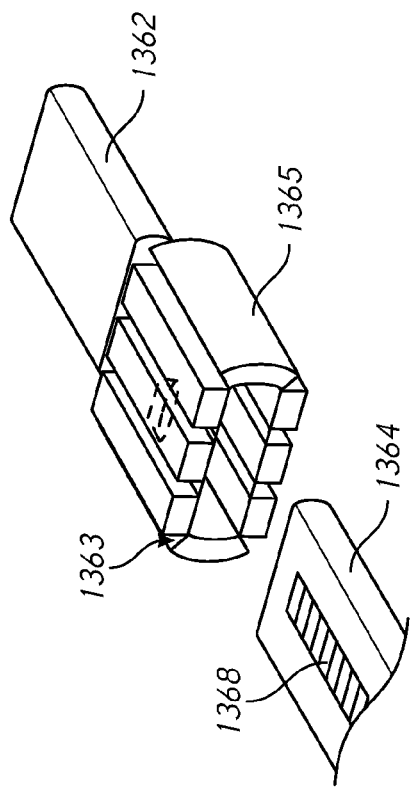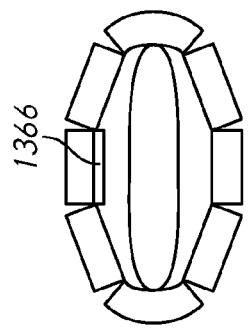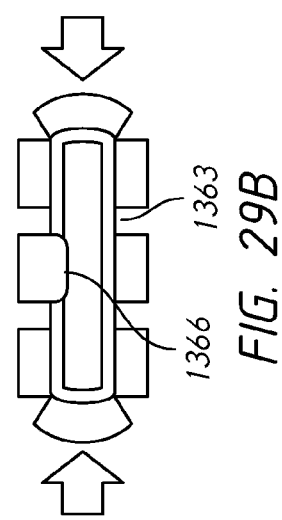
FIG. 29A
FIG. 29B
FIG. 29C

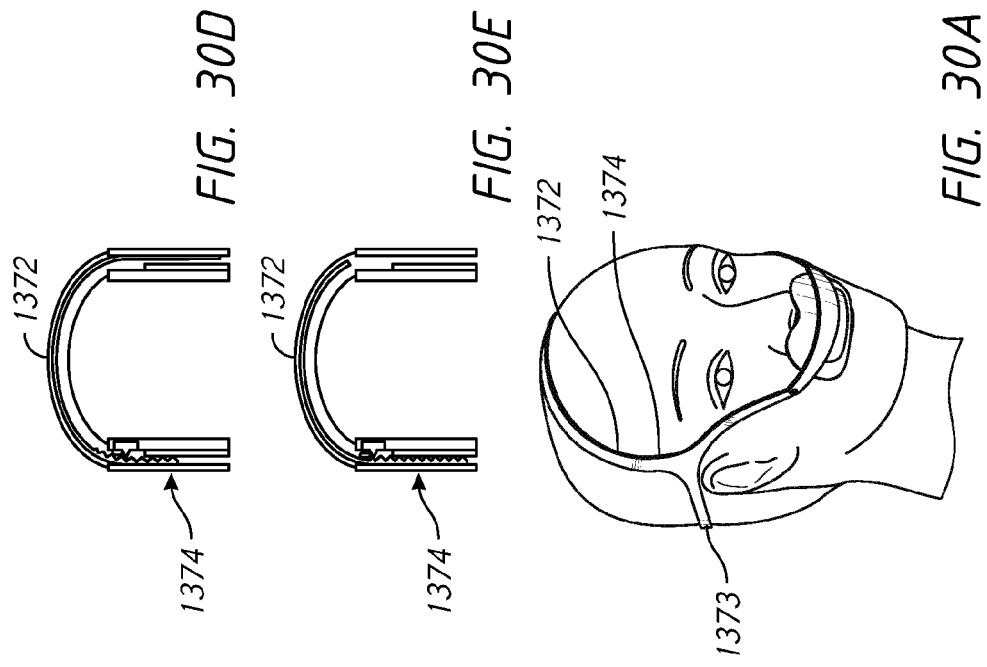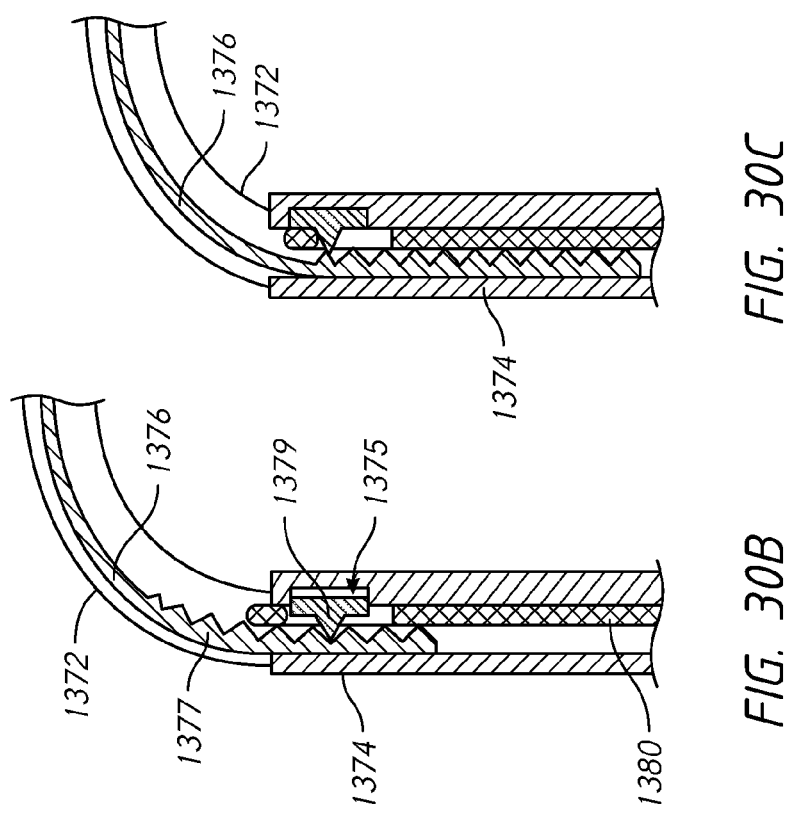

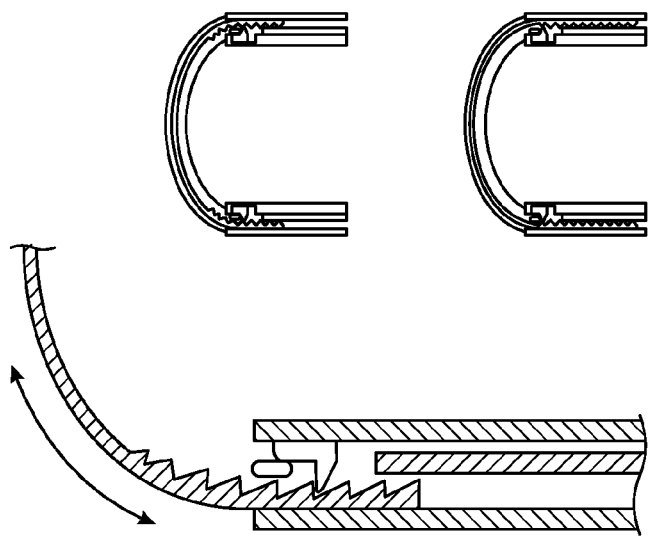
FIG. 30I FIG. 30J
FIG. 30H
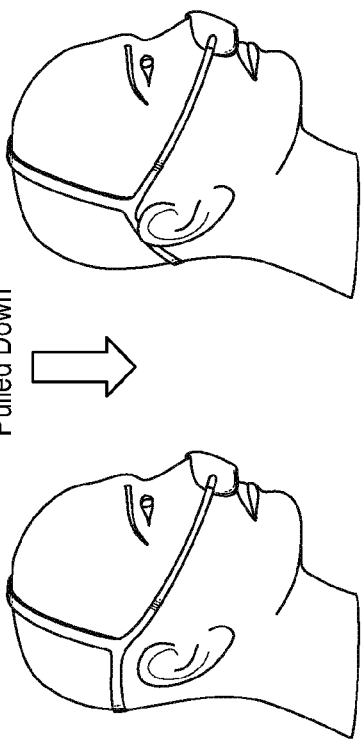
FIG. 30G
FIG. 30F

HEADGEAR ADJUSTMENT MECHANISM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to a headgear assembly for a respiratory mask. More particularly, the present disclosure relates to an adjustment mechanism for a headgear assembly.

Description of the Related Art

Respiratory masks are used to provide respiratory therapies such as, but not limited to, continuous positive airway pressure (CPAP), non-invasive ventilation (NIV) or oxygen therapy to patients or users. In CPAP therapy in particular a respiratory mask is secured to a user's face such that a supply of pressurized air is applied to their airways. A headgear assembly is used to secure the mask to the user's face.

Some headgear assemblies known in the art comprise a plurality of interconnected straps that extend over and around a user's head to secure the respiratory mask. The straps are generally made from a material such as Breath-o-prene® and are flexible and, in some cases, elasticated. The headgear assemblies are usually available in a range of sizes to suit users with differing head sizes. The size of headgear that is provided to a user is usually dictated by the size of the mask that they select.

The size of the headgear assembly can be further adjusted to fit each individual user's head size, via an adjustment mechanism. The adjustment mechanisms used in the prior art headgear assemblies usually include a buckle arrangement such that a pair of headgear straps pass through the buckle and double back on themselves, wherein they are secured in place by a fastener such as Velcro. Adjustment mechanisms such as these provide continuous adjustment and in some configurations form the connection between the mask and the headgear assembly.

BRIEF SUMMARY

In a first aspect of the present disclosure, a headgear for a respiratory mask is provided having an adjustment arrangement comprising a first and a second strap. The first and second straps are configured to overlap and are slideably engaged by a pair of interlocking rails. This arrangement may provide a headgear that is easily adjusted in size.

Preferably, the first and second straps are made of an inelastic material to provide structure to the headgear and prevent, inhibit, or reduce the likelihood of unintentional adjustment of the headgear size Preferably, the rails include a pair of inner rails and a pair of outer rails.

Preferably, the rails include a flange configured to secure the straps together.

Preferably, the adjustment arrangement includes a locking geometry and a lock that are configured to secure the first and second straps in a user defined position such that the headgear may be sized to fit each individual user.

BRIEF DESCRIPTION OF THE DRAWINGS

The present disclosure will now be described by way of example only with reference to the figures, in which:

FIG. 6A shows a perspective view of a third embodiment of an adjustment arrangement of the headgear assembly of FIG. 3.

FIG. 6B shows a cross-sectional view of the adjustment arrangement of FIG. 6A.

FIG. 11C is a side view of a variation of the adjustment arrangement of FIGS. 11A and 11B.

FIG. 13A is a perspective view of another variation of the adjustment arrangement of FIGS. 5A and 5B, including two locks.

FIG. 13B is a cross-sectional view of the second lock of FIG. 13A.

FIG. 14A is a side view of another variation of a locking mechanism.

FIG. 14B is a perspective view of the locking mechanism of FIG. 14A.

FIG. 16A is a longitudinal cross-sectional view of a variation of the adjustment arrangement of FIGS. 4A and 4B including an example embodiment of a locking mechanism in a locked position.

FIG. 16B is a longitudinal cross-sectional view of the locking mechanism of FIG. 16A in an unlocked position.

FIG. 17A is a perspective view of a variation of the adjustment arrangement of FIGS. 4A and 4B including an example embodiment of a locking mechanism in an unlocked position.

FIG. 17B is a longitudinal cross-sectional view of the locking mechanism of FIG. 17A in a locked position.

FIG. 17C is a longitudinal cross-sectional view of the locking mechanism of FIG. 17A in the unlocked position.

FIG. 19A is a longitudinal cross-sectional view of a variation of the adjustment arrangement of FIGS. 4A and 4B including an example embodiment of a locking mechanism in an unlocked position.

FIG. 19B is a longitudinal cross-sectional view of the locking mechanism of FIG. 19A in a locked position.

FIG. 19C is a perspective view of the locking mechanism of FIGS. 19A-19B in the locked position.

FIG. 19D is a bottom view of an alternative embodiment of a pull tab portion of the locking mechanism of FIGS. 19A-19C.

FIG. 20A is a longitudinal cross-sectional view of a variation of the adjustment arrangement of FIGS. 4A and 4B including an example embodiment of a locking mechanism in a locked position.

FIG. 20B is a perspective view of pull tab and pull tab retainer portions of the locking mechanism of FIG. 20A.

FIG. 21A is a longitudinal cross-sectional view of a variation of the adjustment arrangement of FIGS. 4A and 4B including an example embodiment of a locking mechanism in an unlocked position.

FIG. 21B is a longitudinal cross-sectional view of the locking mechanism of FIG. 21A in a locked position.

FIG. 22A is a longitudinal cross-sectional view of a variation of the adjustment arrangement of FIGS. 4A and 4B including an example embodiment of a locking mechanism.

FIG. 22B is a perspective view of the locking mechanism of FIG. 22A.

FIG. 24A is an exploded view of an example embodiment of an adjustment arrangement.

FIG. 24B is a longitudinal cross-section of the assembled adjustment arrangement of FIG. 24A.

FIG. 24C is a longitudinal section view of a variation of the adjustment arrangement of FIGS. 24A-24B.

FIG. 25A is a perspective view of an example embodiment of an adjustment arrangement.

FIG. 25B is a cross-sectional view of the outer rail of the adjustment arrangement of FIG. 25A.

FIG. 25C is a lateral cross-sectional view of the flexible ring of the adjustment arrangement of FIG. 25A.

FIG. 25D is a longitudinal cross-sectional view of the flexible ring of the adjustment arrangement of FIG. 25A.

FIG. 25E shows various shapes for the fins of the flexible ring.

FIG. 25F shows a force profile for the fins in use.

FIG. 26A is a longitudinal section view of an example embodiment of an adjustment arrangement as the strap is adjusted in a first direction.

FIG. 26B is a longitudinal section view of the adjustment arrangement of FIG. 26A as the strap is adjusted in a second, opposite direction.

FIG. 26C is a perspective view of certain components of the adjustment arrangement of FIGS. 26A-26B.

FIG. 27A is a top perspective view of an example embodiment of an adjustment arrangement.

FIG. 27B is a longitudinal cross-sectional view of the adjustment arrangement of FIG. 27A.

FIG. 27C shows force profiles for the adjustment arrangement of FIGS. 27A-27B.

FIG. 27D shows various examples of friction surfaces for the adjustment arrangement of FIGS. 27A-27B.

FIG. 28A is a top perspective view of an example embodiment of an adjustment mechanism.

FIG. 28B is a longitudinal cross-sectional view of the adjustment arrangement of FIG. 28A.

FIG. 28C is a transverse cross-sectional view of the adjustment arrangement of FIGS. 28A-28B in a locked state.

FIG. 28D is a transverse cross-sectional view of the adjustment arrangement of FIGS. 28A-28B in an unlocked state.

FIG. 29A is an exploded top perspective view of an example embodiment of an adjustment mechanism.

FIG. 29B is a transverse cross-sectional view of the example embodiment of the adjustment mechanism of FIG. 29A in a locked state.

FIG. 29C is a transverse cross-sectional view of the example embodiment of the adjustment mechanism of FIG. 29A in an unlocked state.

FIG. 30A shows an example embodiment of a headgear including an adjustment mechanism with the headgear being positioned on a user's head.

FIG. 30B is a longitudinal cross-sectional view showing the adjustment mechanism of the headgear of FIG. 30A in a locked state.

FIG. 30C is a longitudinal cross-sectional view showing the adjustment mechanism in an unlocked state.

FIG. 30D shows a portion of the headgear of FIG. 30A with a strap at a maximum length.

FIG. 30E shows the strap of FIG. 30D at a minimum length.

FIGS. 30F and 30G illustrate loosening of the headgear of FIG. 30A.

FIG. 30H shows an embodiment of the adjustment mechanism for the headgear of FIG. 30A.

FIG. 30I shows a variation of the adjustment mechanism of the headgear of FIG. 30A with the strap at a maximum length.

FIG. 30J shows the adjustment mechanism of FIG. 30I with the strap at a minimum length.

DETAILED DESCRIPTION

Figure 1:
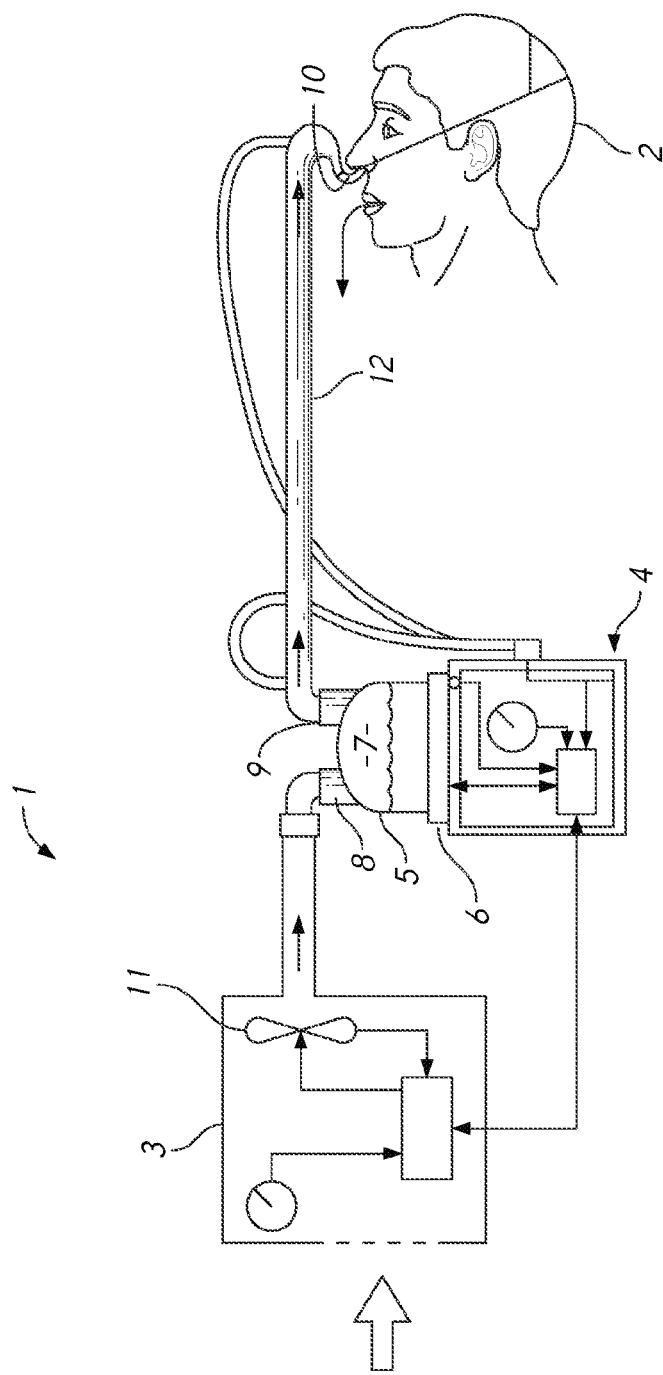
FIG. 1 shows a schematic view of a respiratory therapy system.

FIG. 1 shows a schematic view of a typical respiratory therapy system 1 for providing a stream of heated humidified gases at a pressure above atmospheric to a user 2. The system 1 includes a gases supply unit or blower unit 3, which in use receives gases from atmosphere and passes the gases through a fan unit 11 or similar inside the blower unit 3 so that, when the gases leave the blower unit 3, they are at a pressure above atmospheric and are flowing at a certain flow rate. A humidifier unit 4 is located downstream from the blower unit 3 and in use receives the flow of pressurised gases from the blower unit 3. The humidifier unit 4 includes a water chamber 5, which in use contains a volume of water 7. The volume of water 7 in the chamber 5 is in use heated. In the embodiment shown in FIG. 1, the water 7 is heated by a heater plate 6 located underneath the chamber 5. The gases from the blower unit 3 pass into the chamber 5 via an entry port 8, the gases passing through the chamber 5 and across the surface of the water 7, becoming heated and humidified as they do so. The gases then pass out of the humidifier chamber 5 via a humidifier outlet port 9.

It should be noted that a modular humidification system has been described above. In other words, a system is shown where the humidifier unit 4 is separate from the blower unit 3. An integrated humidification system could also be used. In other words, a system can be used where the blower unit and the humidifier unit are two integral parts of a single unit, or where the blower unit and the humidifier unit are rigidly attached or connected together in use.

Furthermore, it is preferable, although not necessary, that the overall respiratory system have a modular configuration. In some embodiments, the individual components are releasably interconnected to form the complete respiratory system. The modularity of the system allows individual components to be maintained and replaced as necessary. It also permits components to be interchanged to meet individual user requirements. This is particularly useful in institutional applications, where a base unit (such as the blower and humidifier unit) can be used for different recipients at different times while the patient interface is interchanged to suit the particular user.

In use, a main supply conduit 12 is connected to the humidifier outlet 9. The heated and humidified gases stream exits the humidifier unit 4 via the humidifier outlet 9 and enters the main supply conduit 12, passing along the supply conduit 12 to an interface assembly 10 which is connected to a user end of the supply conduit 12.

Figure 2A:
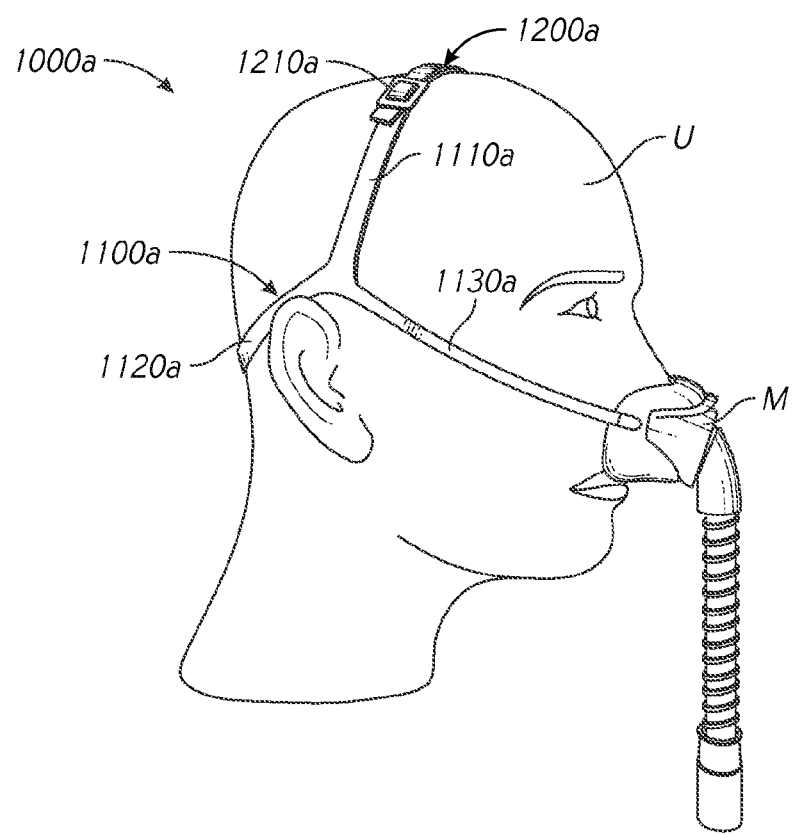
FIG. 2A shows a perspective view of a prior art respiratory mask assembly.
Figure 2B:
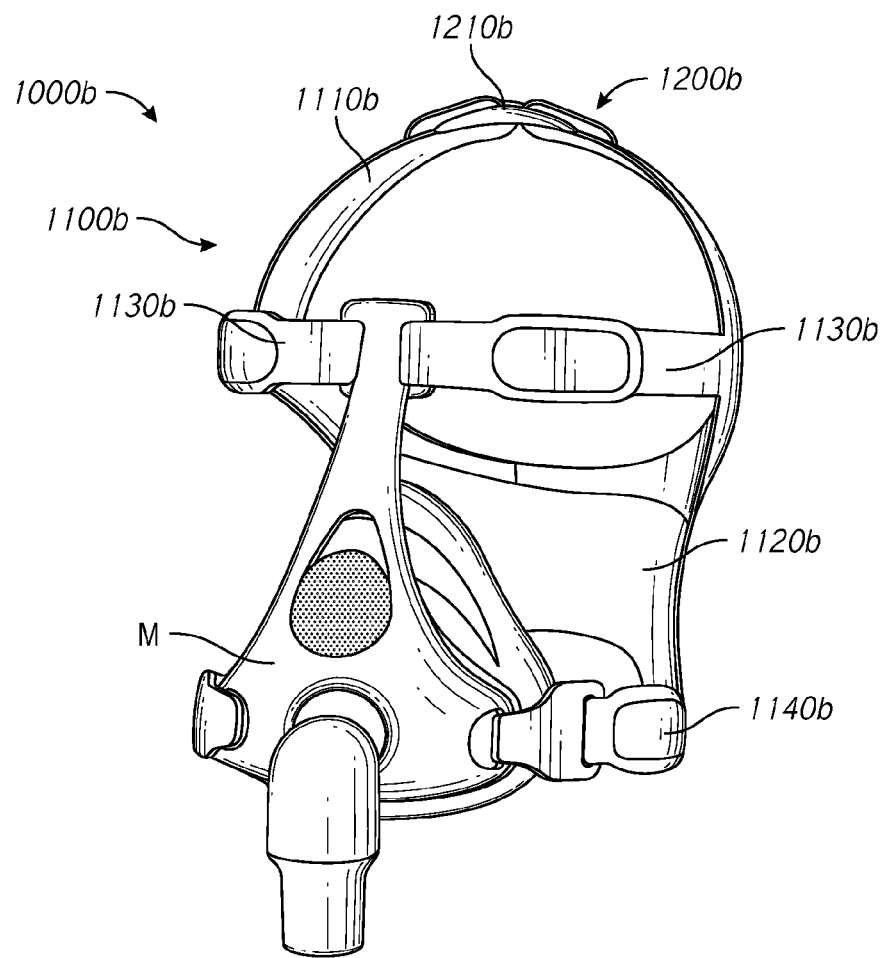
FIG. 2B shows a perspective view of another prior art respiratory mask assembly.

FIGS. 2A and 2B show two embodiments of a respiratory mask assembly 1000a, 1000b. The first mask assembly 1000a comprises a mask M and a headgear assembly 1100a. The headgear assembly 1100a comprises a top strap 1110a and a rear strap 1120a. The ends of the top strap 1110a and the rear strap 1120a are joined together at a junction on each side of a user's head, in use, such that a bifurcated structure is formed. A front strap 1130a extends from each of the junctions of the top and rear straps 1110a, 1120a. The top strap 1110a can comprise two portions that extend upwards over the top of a user's U head and the two portions can be adjustably connected at a midpoint, in use. The rear strap 1120a extends around the rear of a user's head, in use. The front straps 1130a extend forward of the user's ears and across the user's cheeks and the front straps 1130a are configured to connect to the mask M.

The second mask assembly 1000b comprises a mask M and a headgear assembly 1100b. The headgear assembly 1100b comprises a top strap 1110b and a rear strap 1120b. The ends of the top strap 1110b and the rear strap 1120b are joined together at a junction on each side of a user's head, in use, such that a bifurcated structure is formed. A first front strap 1130b extends from the junctions of the top and rear straps 1110b, 1120b and a second front strap 1140b extends from a lower portion of the rear strap 1120b. The top strap 1110b can comprise two portions that extend upwards over the top of a user's U head and the two portions are adjustably connected at a midpoint, in use. The rear strap 1120b extends around the rear of a user's head, in use. The front straps 1130b, 1140b extend forward of the user's ears and across their forehead and cheeks, respectively, and the front straps 1130b, 1140b are configured to connect to the mask M.

The headgear assemblies 1100a, 1100b can be made of a flexible fabric, such as but not limited to BREATH-O-PRENE® brand breathable neoprene fabric composite. In some configurations, the headgear assemblies 1100a, 1100b can include components that are formed of such a material. In some configurations, the headgear assemblies can include components that are formed of an elastic fabric. In some configurations, the headgear assemblies 1100a, 1100b can be made of an elastic fabric.

The size of headgear assemblies 1100a, 1000b can be adjusted by an adjustment arrangement 1200a, 1200b. The adjustment arrangement 1200a, 1200b can be used to modify the size and configuration of the headgear assemblies 1100a, 1100b to better fit the head of a user U. The adjustment arrangements 1200a, 1200b in FIGS. 2A and 2B comprise a buckle 1210a, 1210b through which the two portions of the top straps 1110a, 1110b pass. The top straps 1110a, 1110b are threaded through the buckle 1210a, 1210b and folded back on themselves to store any excess strap length. The top straps 1110a, 1110b can be retained in a user defined position, for example, by friction between the buckle 1210a, 1210b and the top straps 1110a, 1110b or, alternatively or in addition, by a fastening arrangement such as a hook and loop fastener. The size of the headgear assembly 1100a, 1100b can be adjusted by pulling on the ends of the top strap 1110a, 1110b portions such that a length of each portion extends beyond the buckle 1210a, 1210b.

The adjustment arrangement 1200a, 1200b may cause the headgear assembly 1100a, 1100b to be bulky on the user's head. For example, this may be a result of the top straps 1110a, 1110b being folded back on themselves, which doubles the thickness. The bulkiness of the headgear assembly 1100a, 1100b provides some room for improvement to improve the comfort of the user, which can improve the compliance of the user with the treatment.

Figure 3:
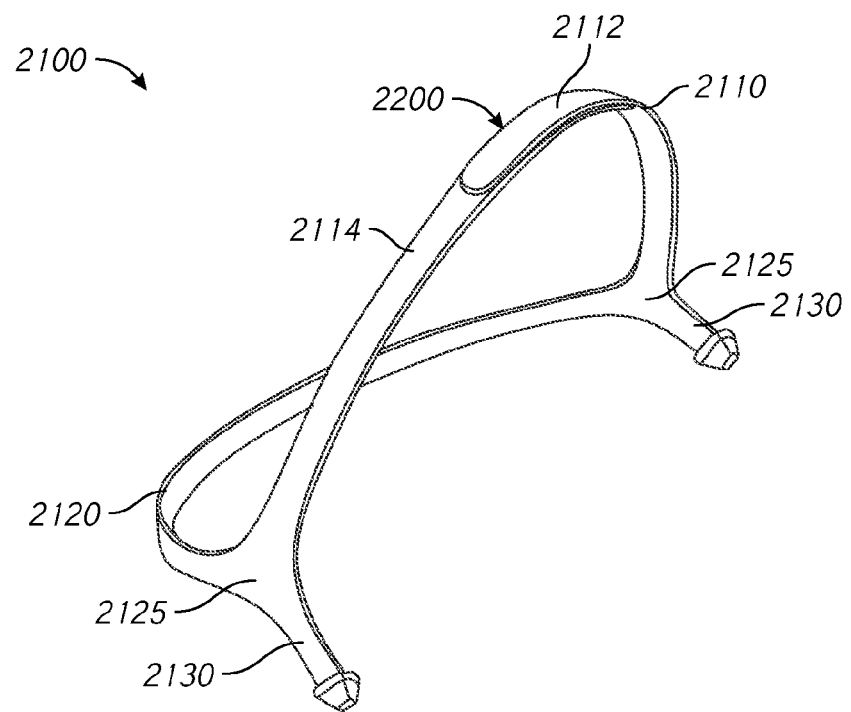
FIG. 3 shows a perspective view of a headgear assembly of the present disclosure.

FIG. 3 shows a non-limiting exemplary embodiment of a headgear assembly 2100 of the present disclosure. The headgear assembly 2100 comprises a top strap 2110 and a rear strap 2120. In the illustrated configuration, the ends of the top strap 2110 and the rear strap 2120 are joined at junctions 2125. In such a configuration, a bifurcated structure is provided. In the illustrated embodiment, the top strap 2110 and the rear strap 2120 are integrally formed, monolithic and/or unitary with each other. A front strap 2130 extends from each of the junctions 2125 and is configured to be attached to a mask (not shown in FIG. 3). The front strap 2130 and the portions of the top strap 2110 and the rear strap 2120 that are directly adjacent to the junctions 2125 form a Y-shape.

The top strap 2110 and the rear strap 2120 comprise elongate and inelastic straps that are flexible (i.e., bendable but generally not extensible) and of a fixed length. The headgear assembly 2100 can be made of (or be mainly made of) a semi-rigid material such as, but not limited to, nylon, polyethylene, polypropylene, or a thermoplastic elastomer such as Arnitel® TPE VT3108 or PEBAX®. In some embodiments, the headgear assembly 2100 may be covered in a fabric skin to improve comfort for the user. The semi-rigid material provides the headgear assembly 2100 with a structure that maintains its shape when not in use, which improves ease of use during donning and doffing. Due to the semi-rigid material, the headgear assembly 2100 may not be able to be adjusted in size in the same way that fabric headgear assemblies (such as the embodiment of FIG. 1) can be. For example, the top strap 2110 may not be flexible enough to pass through a buckle. As such, an adjustment arrangement 2200 that is suitable for semi-rigid headgear assembly 2100 can be provided to allow for improved adjustability.

In the illustrated embodiment, top strap 2110 comprises a first strap 2112 and a second strap 2114, which are adjustably connected by the adjustment arrangement 2200. The adjustment arrangement 2200 allows the first and second straps 2112, 2114 to be secured to each other in an overlapping configuration.

Figure 4A:
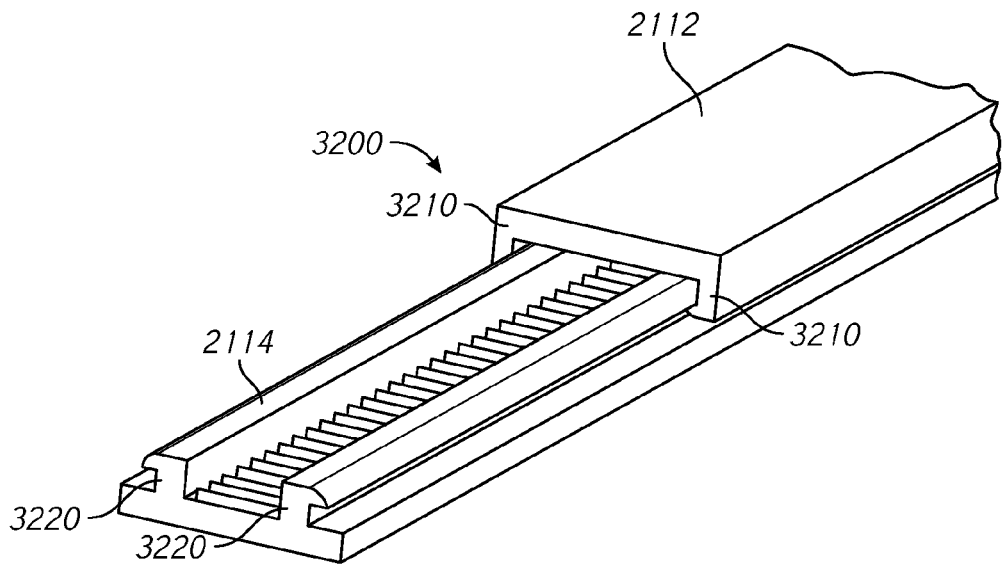
FIG. 4A shows a perspective view of a first embodiment of an adjustment arrangement of the headgear assembly of FIG. 3.
Figure 4B:
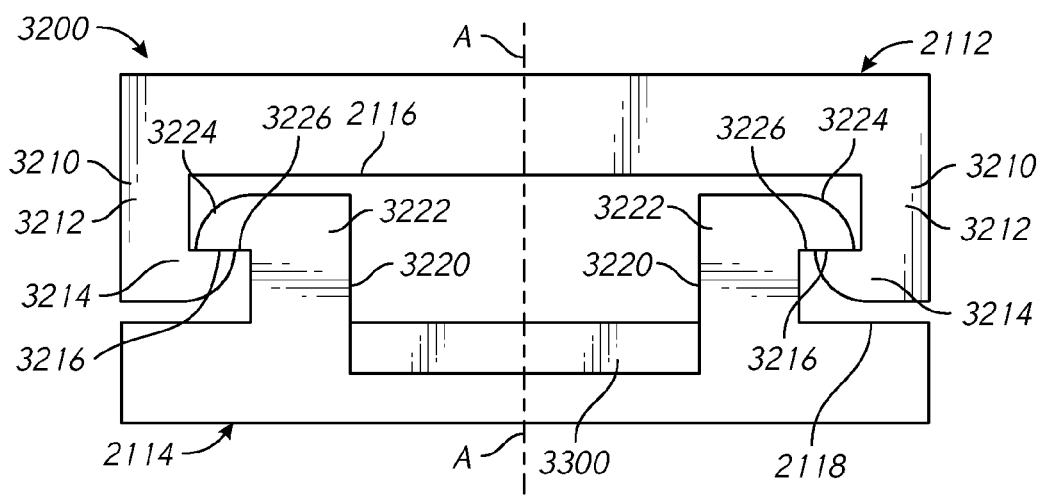
FIGS. 4B and 4C show cross-sectional views of the adjustment arrangement of FIG. 4A.
Figure 4C:
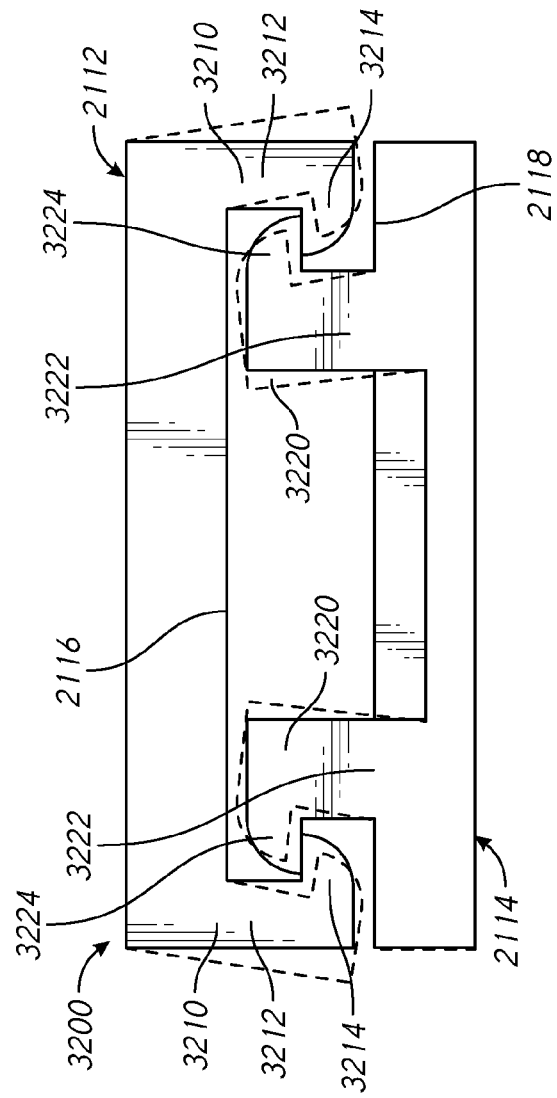

FIGS. 4A to 4C show a first non-limiting exemplary embodiment of an adjustment arrangement 3200, which is configured for use in combination with the headgear assembly 2100. The adjustment arrangement 3200 comprises a pair of outer rails 3210 and a pair of inner rails 3220 that are configured to be interlocking.

The outer rails 3210 are elongate and protrude substantially perpendicularly to an inner surface 2116 of the first strap 2112 (i.e., a surface or side of the first strap 2112 that faces the second strap 2114 in use as shown in FIGS. 4B and 4C). The outer rails 3210 are spaced apart, for example, by the width of the first strap 2112, and extend along at least a portion of the elongate edges of the first strap 2112. The inner rails 3220 are elongate and protrude substantially perpendicularly to an inner surface 2118 of the second strap 2114 (i.e., a surface or side of the second strap 2114 that faces the first strap 2112 in use). The inner rails 3220 extend along at least a portion of the second strap 2114 and are offset from the elongate edges of the second strap 2114. The inner rails 3220 are spaced apart by a distance that is narrower or less than the spacing of the outer rails 3210. As shown, the inner rails 3220 can be spaced from, or positioned inwardly of, the outer edges of the second strap 2114. In alternative embodiments, the first strap 2112 can comprise the inner rails 3220, and the second strap 2114 can comprise the outer rails 3210.

Each of the outer and inner rails 3210, 3220 comprises an elongate beam 3212, 3222 extending substantially perpendicularly to the inner surface 2116, 2118 of the first strap 2112 or the second strap 2114, respectively. Each of the outer and inner rails 3210, 3220 has a flange 3214, 3224 at an end of the beam 3212, 3222 distal to or opposite from the inner surfaces 2116, 2118 of the first and second straps 2112, 2114. The beams 3212, 3222 can comprise a substantially rectangular cross-section. The flanges 3214 of the first strap 2112 project inwardly from the beams 3212 towards the center of the first strap 2112. The flanges 3224 of the second strap 2114 project outwardly from the beams 3222 towards the edges of the second strap 2114.

In use, the inner surfaces 2116, 2118 of the first and second straps 2112, 2114 are configured to face each other such that the outer and inner rails 3210, 3220 oppose each other and the inner rails 3220 are positioned between the outer rails 3210. The flanges 3214 of the outer rails 3210 are configured to engage with or contact the flanges 3224 of the inner rails 3220, in use, forming a retaining feature that secures the first and second straps 2112 and 2114 together in an overlapping arrangement.

Each of the flanges 3214, 3224 has an underside 3216, 3226. The undersides 3216 of the first strap 2112 are configured to overlap with and contact the undersides 3226 of the second strap 2114. The application of a tension force perpendicular to the width and length of the straps 2112, 2114 causes the undersides 3216, 3226 to be engaged until the force is great enough to cause the beams 3212, 3222 to deflect away from each other to allow the flanges 3214, 3224 to move past each other, as shown in FIG. 4c. Application of a sufficient tension force can allow the straps 2112, 2114 to be separated from each other. The dashed lines in FIG. 4C indicate the deformed state of the rails 3210, 3220, when the straps 2112, 2114 are pulled away from each other. The geometry of the outer and inner rails 3210, 3220, along with the material they are made of, can be such that the beams 3212, 3222 require a large force to deflect. This may inhibit or help reduce the likelihood of unintentional separation of the straps 2112, 2114 during use.

The rails 3210, 3220 are configured to align the first and second straps 2112, 2114 with each other. The rails 3210, 3220 allow the first and second straps 2112, 2114 to slide relative to each other. The size of the headgear 2100 can be adjusted by sliding the first and second straps 2112, 2114 relative to each other. The length of the straps 2112, 2114 that is overlapped determines the overall length of the top strap 2110.

The tolerance and/or clearance between the flanges 3214, 3224 of the outer and inner rails 3210, 3220 determine the amount of friction between the outer and inner rails 3210, 3220. The friction between the outer and inner rails 3210, 3220 influences the ease with which the first and second straps 2112, 2114 can be slid relative to each other. In some embodiments, the friction force can be sufficient to retain the first and second straps 2112, 2114 in a user-defined position during use of a respiratory mask. This allows the size of the headgear assembly 2100 to remain constant until the user intentionally adjusts the amount of overlap between the first and second straps 2112, 2114.

Figure 5A:
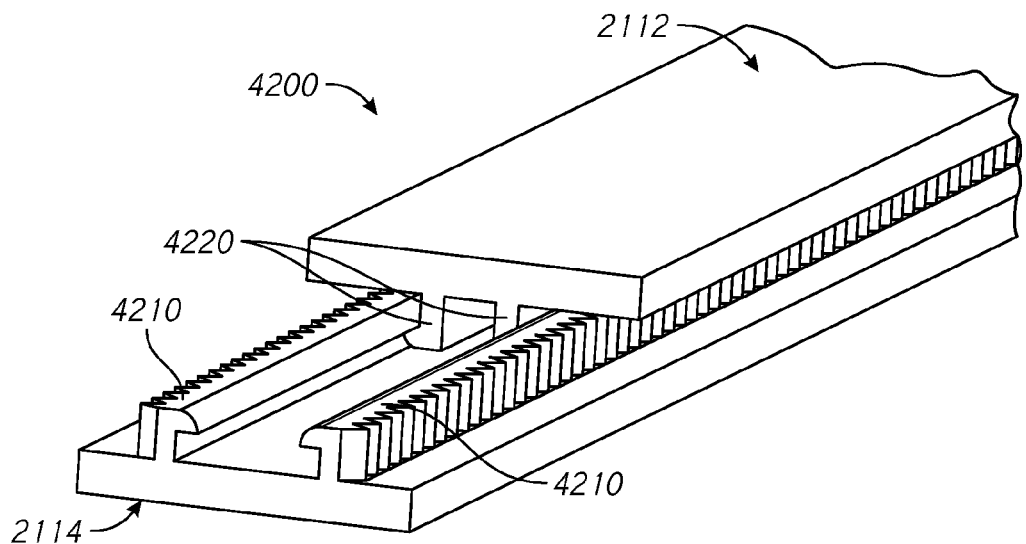
FIG. 5A shows a perspective view of a second embodiment of an adjustment arrangement of the headgear assembly of FIG. 3.
Figure 5B:
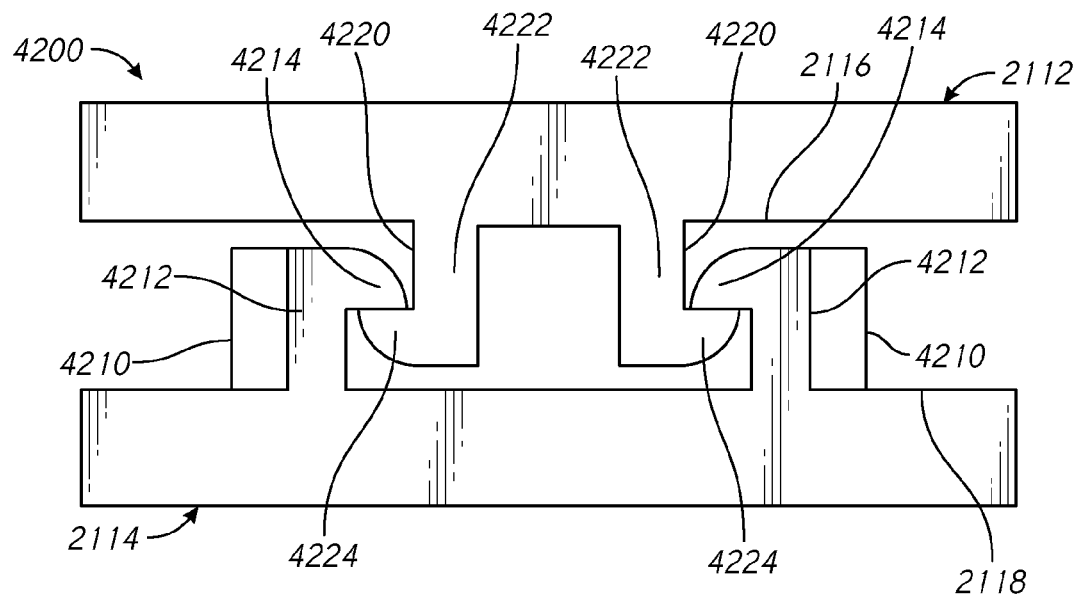
FIG. 5B shows a cross-sectional view of the adjustment arrangement of FIG. 5A.

FIGS. 5A and 5B show another non-limiting exemplary embodiment of an adjustment arrangement 4200, which is configured for use in combination with headgear assembly 2100. The adjustment arrangement 4200 is similar to the adjustment arrangement 3200 described above in some ways and is positioned between a first and second strap 2112, 2114. The first strap 2112 includes a pair of inner rails 4220 that protrude perpendicularly from an inner surface 2116 of the first strap 2112. The second strap 2114 includes a pair of outer rails 4210 that protrude perpendicularly from an inner surface 2118 of the second strap 2114. The first and second straps 2112, 2114 are arranged such that they overlap and the outer and inner rails 4210, 4220 oppose each other between the straps 2112, 2114. In alternative embodiments, the first strap 2112 can include a pair of outer rails 4210 and the second strap 2114 can include a pair of inner rails 4220 in addition or as an alternative to the provision of the rails 4120, 4220.

The outer and inner rails 4210, 4220 comprise the elongate beams 4212, 4222 that have a flange 4214, 4224 on an end distal to or opposite of the inner surfaces 2116, 2118 of the first and second straps 2112, 2114. The rails 4210, 4220 extend along at least a portion of the length of the first and second straps 2112, 2114. In the illustrated embodiment, the outer rails 4210 are offset from the edges of the second strap 2114. The inner rails 4220 are spaced apart by a width that is narrower than the outer rails 4210. The flanges 4214 of the outer rails 4210 extend substantially perpendicular to the beams 4212 and inwardly towards the center of the strap 2114. The flanges 4224 of the inner rails 4220 extend substantially perpendicular to the beams 4222 and outwardly away from the center of the strap 2112.

The rails 4210, 4220 are configured to align the first and second straps 2112, 2114 with each other. They allow the first and second straps 2112, 2114 to slide relative to each other. The size of the headgear 2100 can be adjusted by sliding the first and second straps 2112, 2114 relative to each other. The length of the straps 2112, 2114 that is overlapped determines the overall length of the top strap 2110.

The tolerance and/or clearance between the flanges 4214, 4224 of the outer and inner rails 4210, 4220 determine the amount of friction between the outer and inner rails 4210, 4220. The friction between the outer and inner rails 4210, 4220 influences the ease with which the first and second straps 2112, 2114 can be slid relative to each other. In some embodiments the friction force can be sufficient to retain the first and second straps 2112, 2114 in a user defined position during use of a respiratory mask. This allows the size of the headgear assembly 2100 to remain constant until the user intentionally adjusts the amount of overlap between the first and second straps 2112, 2114.

FIGS. 6A and 6B show another non-limiting exemplary embodiment of an adjustment arrangement 5200 that is configured for use in combination with the headgear assembly 2100. The first strap 2112 comprises a single inner rail 5220 and the second strap 2114 comprises a pair of outer rails 5210. The outer rails 5210 can comprise a beam 5212 and flange 5214, which is similar to the embodiment shown in FIGS. 4A-4C.

The inner rail 5220 comprises a central support beam 5222 and a head that forms a pair of flanges 5224 extending from either side of the central support beam 5222. The central support beam 5222 can have a rectangular cross-section that protrudes from the inner surface 2116 of the first strap 2112. In other embodiments, the cross-section may be any other appropriate shape, including, but not limited to, a trapezium. The central support beam 5222 extends along at least a portion of the length of the first strap 2112. The flanges 5224 extend outwardly perpendicular from the sides of the beam 5222 and are configured to engage with or contact the flanges 5214 of the second strap 2114, in use. In some alternative embodiments, the second strap 2114 can comprise the single inner rail 5220 and the first strap 2112 can comprise the pair of outer rails 5210.

The beams 5212 and central support beam 5222 are configured to align and connect the first and second straps 2112, 2114 to each other. They allow the first and second straps 2112, 2114 to slide relative to each other. The size of the headgear 2100 can be adjusted by sliding the first and second straps 2112, 2114 relative to each other. The length of the straps 2112, 2114 that is overlapped determines the overall length of the top strap 2110.

The tolerance and/or clearance between the flanges 5214, 5224 of the outer and inner rails 5210, 5220 determine the amount of friction between the outer and inner rails 5210, 5220. The tips of the flanges 5214, 5224 can engage with the beams 5212, 5222 to generate friction, as shown in FIG. 6B. The friction between the outer and inner rails 5210, 5220 influences the ease with which the first and second straps 2112, 2114 can be slid relative to each other. In some embodiments, the friction force can be sufficient to retain the first and second straps 2112, 2114 in a user defined position during use of the respiratory mask. This allows the size of the headgear assembly 2100 to remain constant until the user intentionally adjusts the amount of overlap between the first and second straps 2112, 2114.

Figure 7A:
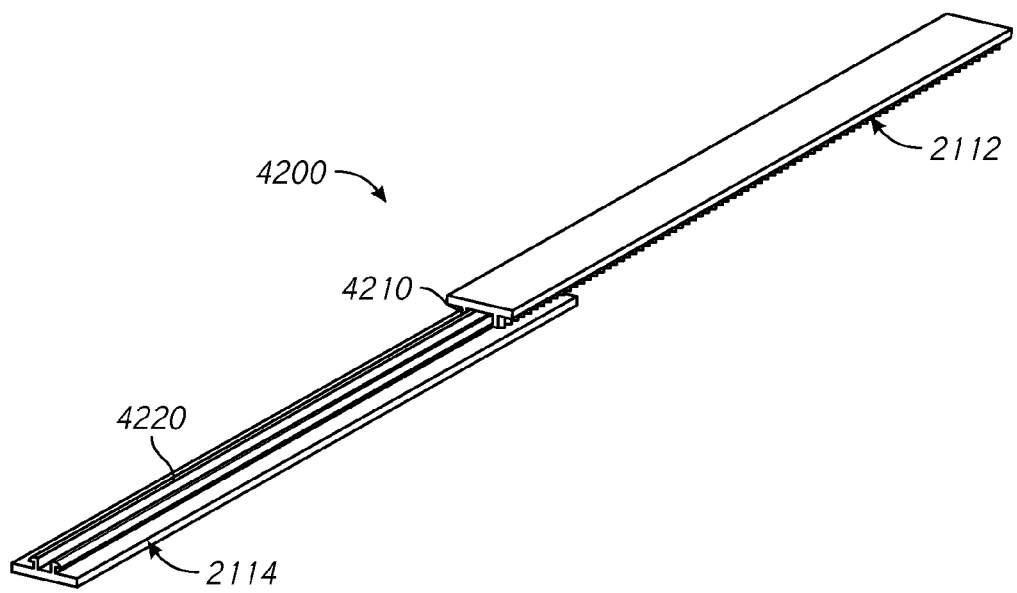
FIGS. 7A and 7B show perspective views of the adjustment arrangement of FIGS. 5A and 5B in differing positions.
Figure 7B:
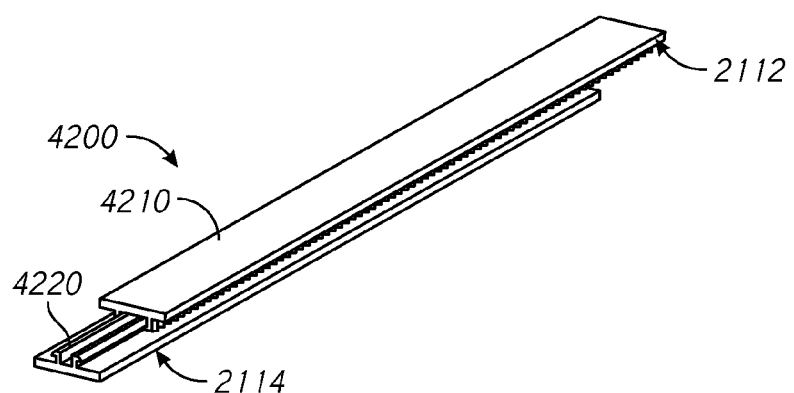
Figure 7C:
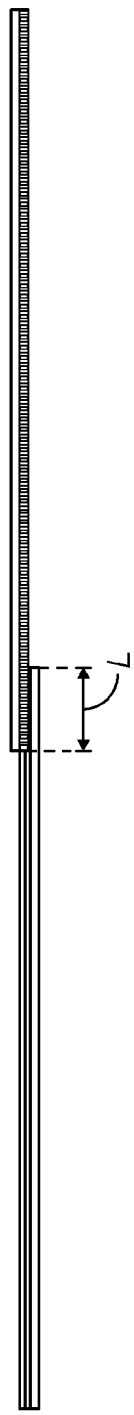
FIGS. 7C to 7E show side views of the adjustment arrangement of FIGS. 5A and 5B in differing positions.
Figure 7D:
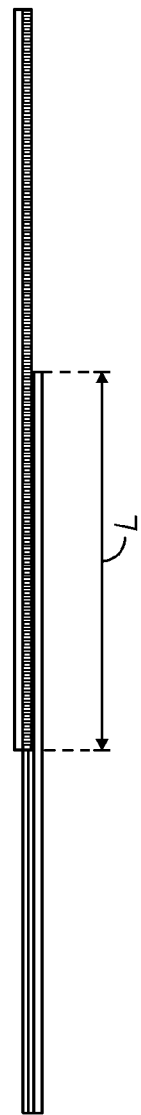
Figure 7E:
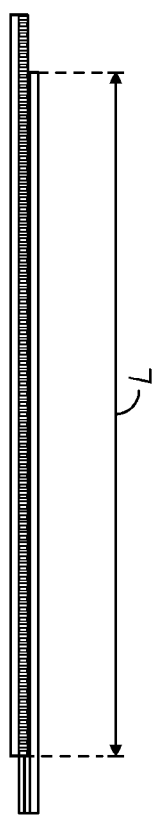

FIGS. 7A to 7E show the first and second straps 2112, 2114 of the adjustment arrangement 4200 of FIGS. 5A and 5B. The straps 2112, 2114 include a pair of outer rails 4210 and inner rails 4220 that are overlapping by differing amounts to provide differing headgear sizes. FIGS. 7A and 7C show the straps 2112, 2114 in a fully extended position wherein the length of the top strap 2110 is maximized and the length of overlap L is minimized. The straps 2112, 2114 are shown in a fully retracted position in FIGS. 7B and 7E. In the fully retracted position, the top strap 2110 length is minimized and the length L of overlap between the first and second straps 2112, 2114 is maximized, such that the size of the headgear is minimized. The adjustment arrangement 4200 can be positioned such that the length L of overlap between the straps 2112, 2114 is anywhere between the minimum and maximum, as shown in FIG. 7D.

Figure 8:
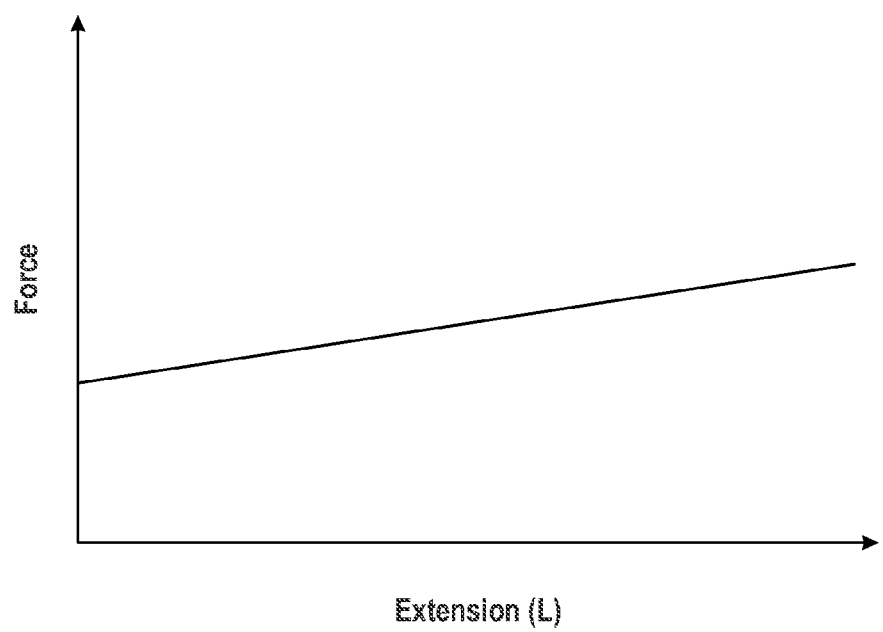
FIG. 8 shows a force extension plot for the adjustment arrangement of FIGS. 5A and 5B.

FIG. 8 shows a force extension plot for the adjustment arrangement 4200 of FIGS. 5A, 5B and 7A to 7E. As the length L of overlap between the straps 2112, 2114 increases, the frictional forces between the outer and inner rails 4210, 4220 increase. This may make it more difficult to adjust the length of the top strap 2110 to a smaller size or may hold the user defined position of the straps 2112, 2114 more securely when the headgear is smaller.

Whilst the effect of the length of overlap between straps has been described in relation to the embodiment of FIGS. 5A and 5B, it should be understood that the same principal applies to any of the other embodiment described herein where there is friction between the outer and inner rails that restricts sliding.

In some embodiments, a locking mechanism can be used to lock the first and second straps 2112, 2114 to each other in a user defined position such that the size of the headgear assembly 2100 is fixed in use. A locking mechanism may reduce the occurrence of unintentional adjustments or creep of the size of the headgear during use. Moreover, the use of a locking mechanism can allow the amount of friction during adjustment to be reduced while creating stability in the adjusted length when adjustment is not sought. Accordingly, the relationship described above between the length of the overlap and the amount of friction can have a reduced impact on use of the headgear assembly.

Figure 9:
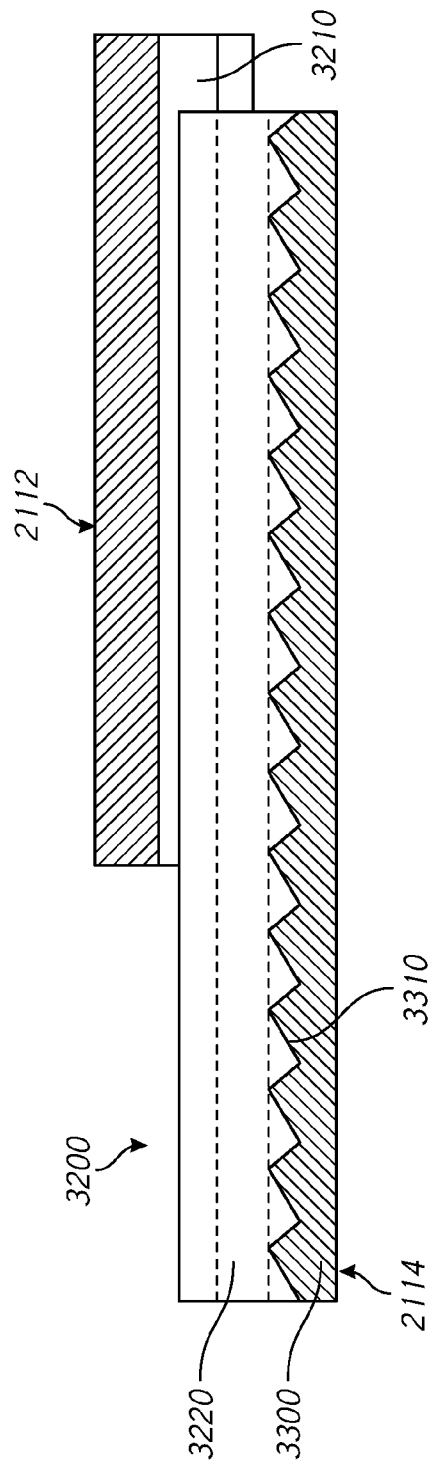
FIG. 9 shows a cross-sectional view of the adjustment arrangement of FIGS. 4A and 4B.

FIG. 9 shows a cross-sectioned view of adjustment arrangement 3200 (shown in figures FA-FC). The second strap 2114 further comprises a locking geometry 3300. The locking geometry 3300 comprises a plurality of notches 3310. In the illustrated embodiment, the notches 3310 are positioned on the inner surface 2118 of the second strap 2114. In some configurations, the notches 3310 are positioned between the inner rails 3220. The notches 3310 can extend across the strap 2114 perpendicularly to the length of the inner rails 3220. The notches 3310 are configured to engage with a corresponding lock.

Figure 10:
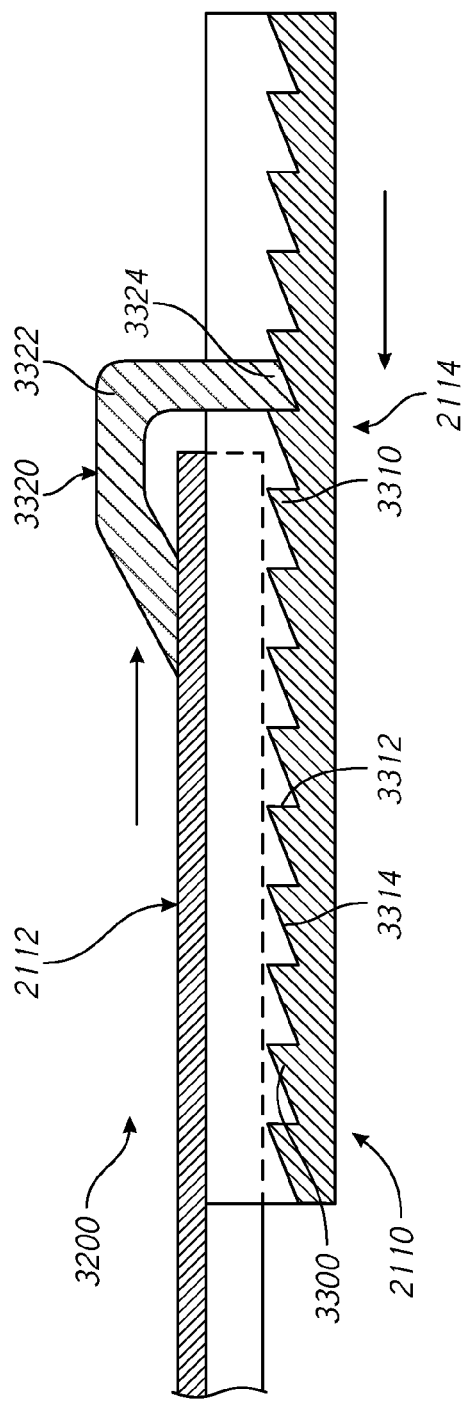
FIG. 10 shows a variation of the adjustment arrangement of FIGS. 4A and 4B including a lock.

FIG. 10 shows a non-limiting exemplary embodiment of a lock 3320 that is configured for use with the notches 3310 of the adjustment arrangement 3200. The lock 3320 is attached to the first strap 2112 and comprises a cantilevered arm 3322 that forms a tooth 3324 at one end. The tooth 3324 is configured to engage with the notches 3310 in a ratchet-like arrangement such that shortening the top strap 2110 length is easier than elongating it. In some configurations, shortening the top strap 2110 and lengthening the stop strap 2110 are resisted equally.

The notches 3310 comprise a steep side 3312 and a shallow side 3314. The shallow side 3314 forms a ramp and the steep side 3312 forms a stop. In the illustrated configuration, when the top strap 2110 is shortened by moving the straps 2112, 2114 in the directions indicated by the arrows, the cantilevered arm 3322 flexes away from the locking geometry 3300 as the tooth 3324 moves up the shallow side 3314. Moving the straps 2112, 2114 in the opposite direction results in the tooth 3324 engaging with the steep side 3312 and locking the length of the top strap 2110.

Figure 15A:
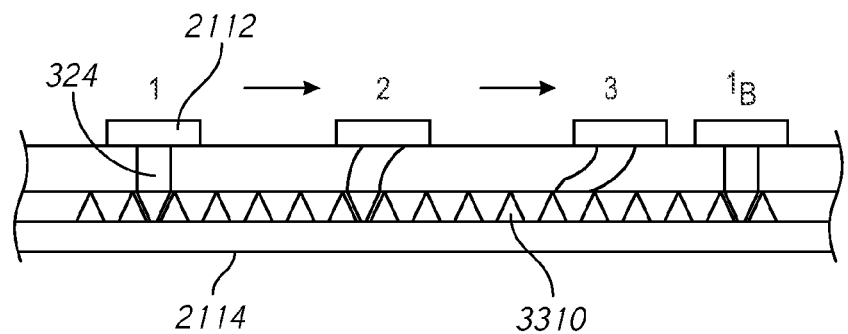
FIG. 15A is a longitudinal cross-sectional view of a variation of the adjustment arrangement of FIGS. 4A and 4B including an example embodiment of a locking mechanism.

FIG. 15A shows another example embodiment of a locking mechanism that can be used with locking geometry. In some configurations, the locking geometry can be the notches 3310 of the adjustment arrangement 3200. In the embodiment of FIG. 15A, the notches 3310 are generally triangular. The locking mechanism comprises a flexible tooth 324 extending from the first strap 2112. The tooth 324 engages or contacts the notches 3310 to resist movement of the straps 2112, 2114 relative to each other. At least one of the tooth 324 and/or the notches 3310 can deflect to allow controlled movement. In some configurations, the tooth 324 flexes to pass over the tops, pinnacles or peaks of the notches to allow for elongation or shortening of the length of the strap 2110 when a user applies enough force to reach a yield force of the tooth 324.

Figure 15B:
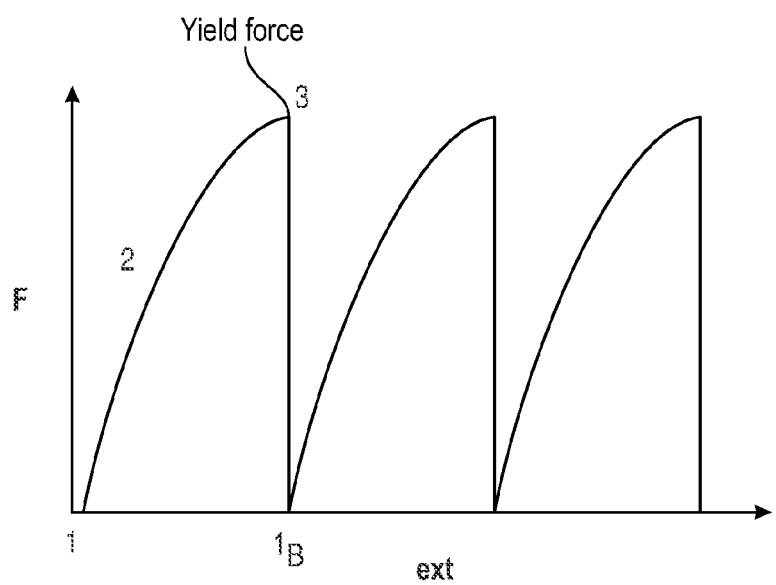
FIG. 15B is a force profile of the locking mechanism of FIG. 15A.

FIG. 15A shows the tooth 324 in four different positions. FIG. 15B shows a graph of the force applied at each of these four different positions. In position 1, no force is applied and the tooth 324 is at rest between two adjacent notches 3310, thereby locking the straps 2112, 2114 relative to each other. As the user begins to apply force to the first strap 2112 and the tooth 324, the tooth 324 begins to flex, which is shown in position 2. When the user applies enough force to reach the yield force of the tooth 324, the tooth 324 flexes sufficiently to be able to side over the tops of the notches 3310, which is shown in position 3. When the force is removed, the tooth 324 returns to rest between another two adjacent notches 3310, which is shown in position 1a.

The tooth 324 can be integrally formed with or coupled to the first strap 2112. The tooth 324 can be made of a different material than the strap 2112. In some embodiments, the tooth 324 is made of a material such as silicone or a TPE. The tooth 324 can be over-molded onto the strap 2112. In some embodiments in which the tooth 324 is a separate component from and coupled to the first strap 2112, the tooth 324 can be coupled to the first strap 2112 in a fixed orientation or in a moveable orientation (e.g., hinged to the first strap 2112 via a secondary component). In some embodiments, the locking mechanism comprises a plurality of teeth 324. Including multiple teeth 324 can increase an overall friction force between the locking mechanism and the notches 3310.

In various embodiments having a locking mechanism that engages or contacts locking geometry, such as the notches 3310 of the adjustment arrangement 3200, such as the cantilevered arm 3322 and tooth 3324 of FIG. 10 and the tooth 324 of FIG. 15A, the tooth 3324, 324 (or portion of the locking mechanism that engages or contacts the notches 3310) can have various tip geometries. For example, FIG. 15C illustrates an embodiment of a locking geometry 3300 having notches 3310 that have a steep side and a shallow side like the notches 3310 shown in the embodiment of FIG. 10. The tooth 3324 of the embodiment of FIG. 15C has a corresponding tip shape that corresponds to the shape of the notches 3310. That is, the tooth 3324 has a shallow surface 314 that corresponds to, contacts, and can slide along the shallow side 3314 of the notches 3310 to allow the straps 2112, 2114 to slide relative to each other in a first direction. The tooth 3324 also has a steep surface 312 that corresponds to and contacts the steep side 3312 of the notches to inhibit movement of the straps 2112, 2114 relative to each other in the opposite direction. Such a configuration can act as a ratchet and can bias movement of the straps 2112, 2114 in one direction so that it is easier to elongate the length of the strap 2110 rather than to shorten it or vice versa. A tooth 324 having the shape shown in FIG. 15C and notches 3310 having the shape shown in FIGS. 10 and 15C can be used in, for example, an embodiment having a lock 3320 that includes a cantilevered arm 3322 as shown in FIG. 10 or an embodiment in which the tooth 324 is integrally formed with or coupled to the first strap 2112 as shown in the embodiment of FIG. 15A.

Figure 15D:
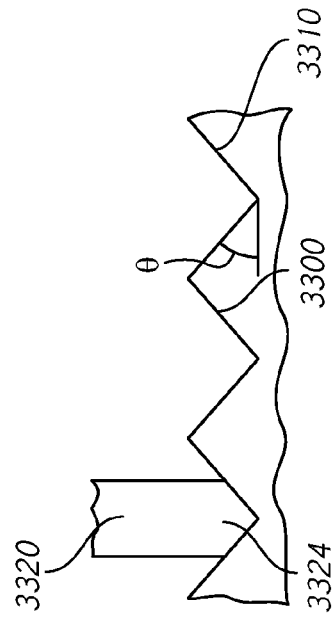
FIGS. 15C and 15D are variations of locking mechanisms that can be used in the adjustment arrangement of FIGS. 4A, 4B, and 15A.
Figure 15C:
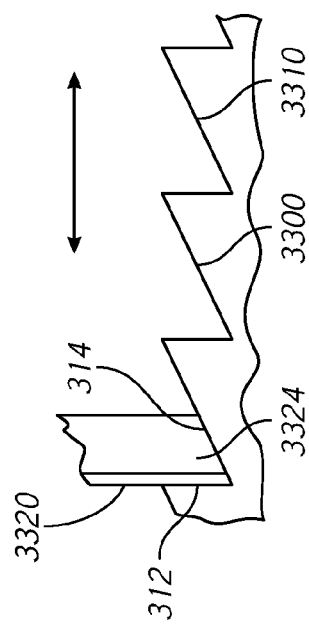

FIGS. 15A and 15D illustrate embodiments of a locking geometry 3300 having notches 3310 that have generally symmetrical triangular shapes. In other words, both sides of the notches 3310 in the embodiments of FIGS. 15A and 15D are shallow. In these embodiments, the tooth 324 has a tip shape that corresponds to the generally symmetrical triangular notches 3310. In other words, the tip of the tooth 324 is generally symmetrical and has two shallow surfaces that contact adjacent shallow surfaces of adjacent notches 3310. Such a configuration can resist or allow movement of the straps 2112, 2114 relative to each other in both directions generally equally. A tooth 324 having the shape shown in FIG. 15D and notches 3310 having the shape shown in FIGS. 15A and 15D can be used in, for example, an embodiment having a lock 3320 that includes a cantilevered arm 3322 as shown in FIG. 10 or an embodiment in which the tooth 324 is integrally formed with or coupled to the first strap 2112 as shown in the embodiment of FIG. 15A.

In other embodiments, the notches 3310 and the teeth 3324, 324 can have shapes between those shown in FIGS. 15C and 15D. For example, the notches 3310 can have two shallow, sloping sides that are asymmetrical. Such a configuration may allow movement of the straps 2112, 2114 relative to each other in either direction but may allow movement in one direction more easily than the other. Angles of the sides of the notches 3310 can be varied to tune the resistance to elongation and/or shortening of the strap 2110.

FIGS. 16A and 16B show a variation of a locking mechanism 420 including a tooth 424 that engages or contacts a locking geometry 420 having the notches 3310. The tooth 424 is part of or coupled to a cantilevered arm 422. The tooth 424 and the notches 3310 can have various shapes as discussed above with respect to the embodiments shown in FIGS. 10-10E. The arm 422 is attached, permanently or removably, to the first strap 2112 and the tooth 424 extends through an aperture 2113 in the first strap 2112 to reach the notches 3310. The arm 422 and/or the tooth 424 can be biased, for example, by virtue of their material and/or shape toward a locked position, which is shown in FIG. 16A in which the tooth 424 engages or contacts the notches 3310. The locking mechanism 420 includes a pull tab 426 attached to the arm 422 and/or the tooth 424. In use, the user can grip and pull the pull tab 426 away from the strap 2112 to lift or bend the arm 422 and/or the tooth 424 and to disengage the tooth 424 from the notches 3310, which is shown in FIG. 16B. In this unlocked position, the straps 2112, 2114 can be moved relative to each other to adjust the length of the strap 2110. In some embodiments, pulling the pull tab 426 can cause the tooth 424 to completely disengage from the notches 3310 such that the straps 2112, 2114 can be moved relative to each other equally easily in either direction. In other embodiments, pulling the pull tab 426 can cause the tooth 424 to only partially disengage from the notches 3310 and can allow the tooth 424 to slide along the tops of the notches 3310 (for example, similar to the embodiment of FIG. 15A). In such an embodiment, the shape of the tooth 424 and the notches 3310 can be selected to resist movement of the straps 2112, 2114 relative to each other more in one direction compared to the opposite direction. The pull tab 426 can advantageously be intuitive for the user to grip and allow the user to make adjustments to the headgear assembly more simply and easily.

In some embodiments, the pull tab 426 is elastic such that the pull tab 426 must be stretched to a lock-out point or maximum extension before the pull tab 426 can lift the arm 422 and/or the tooth 424 to disengage the tooth 424 from the notches 3310. An elastic pull tab 426 that must be stretched to the lock-out point can provide the user with haptic feedback to enable the user to better make intentional adjustments to the length of the strap 2110 and to avoid or reduce the likelihood of making unintentional adjustments. The elastic pull tab 426 creates a delay between when a user initially grips the pull tab 426 and when the tooth 424 is disengaged from the notches 3310 and typically requires an intentional input of sufficient force to reach the lock-out point, which can advantageously prevent, inhibit, or reduce the likelihood of unintentional disengagement and/or unintentional adjustment.

FIGS. 17A-17C show another variation of a locking mechanism including a cantilevered arm 522 with a flexible tooth 524 that engages or contacts a locking geometry 520 having the notches 3310. The tooth 524 and the notches 3310 can have various shapes as described herein with respect to other embodiments. The arm 522 and the tooth 524 can be integrally formed with or coupled to the first strap 2112 and can extend beyond the free end of the first strap 2112. The arm 522 and/or the tooth 524 can be biased toward a locked position in which the tooth 524 contacts the notches 3310, for example, due to the material and/or the shape of the arm 522 and/or the tooth 524. In this embodiment, the locking mechanism includes a pivoting pull tab 526 and a pull tab retainer or movement restrictor 528. An axle or cross-bar 527 couples the pull tab 526 to the first strap 2112 and passes beneath the cantilevered arm 522. The cross-bar 527 can be integrally formed with or can be coupled to the pull tab 526 and/or the first strap 2112. The pull tab retainer 528 has an arched shape or structure and an aperture 529. The arched shape allows the pull tab retainer 528 to sit over or across the cross-bar 527 and the aperture 529 provides clearance for flexing of the tooth 524. In some embodiments, the pull tab 526 can include an aperture to accommodate the pull tab retainer 528 and/or the arm 522 and/or the tooth 524.

In use, the user grips and lifts the pull tab 526, which causes the cross-bar 527 to contact and lift the arm 522 such that the tooth 524 disengages from the notches 3310 (shown in FIG. 17C with the pull tab 526 removed for clarity) and the straps 2112, 2114 can be moved relative to each other. The pull tab 526 can advantageously be intuitive for the user to grip and may be similar to a zipper. The tooth 524 and the locking and unlocking functionality can be somewhat hidden in this embodiment, for example, by the pull tab retainer 528 and/or pull tab 526, because pulling on the pull tab 526 to make adjustments is generally intuitive to the user and the user is unlikely to need to see the full locking mechanism to understand how to adjust the strap length. In some embodiments, the pull tab 526 can be pulled by the user in either direction to disengage the tooth 524 from the notches 3310 and to allow movement of the straps 2112, 2114 in either direction relative to each other to shorten or length the length. In some embodiments, pulling the pull tab 526 can cause the tooth 524 to completely disengage from the notches 3310 such that the straps 2112, 2114 can be moved relative to each other equally easily in either direction. In other embodiments, pulling the pull tab 526 can cause the tooth 524 to only partially disengage from the notches 3310 and allow the tooth 524 to slide along the tops of the notches 3310 (for example, similar to the embodiment of FIG. 15A). In such an embodiment, the shape of the tooth 524 and/or the notches 3310 can be selected to resist movement of the straps 2112, 2114 relative to each other more in one direction than in the opposite direction.

FIGS. 18A-18F show another variation of a locking mechanism, which includes a cantilevered arm 622 with a flexible tooth 624 (see FIG. 18C) that engages or contacts a locking geometry 620 having the notches 3310. The tooth 624 and the notches 3310 can have various shapes as described herein with respect to other embodiments. The arm 622 and the tooth 624 can be integrally formed with or can be coupled to the first strap 2112 and extend beyond the free end of the first strap 2112. The arm 622 and/or the tooth 624 can be biased toward a locked position in which the tooth 624 contacts the notches 3310, such as that shown in FIGS. 18A-18C, for example, due to the material and/or the shape of the arm 622 and/or tooth 624. In the locked position, the tooth 624 can have a height that is greater than a distance between the end of the arm 622 adjacent to or coupled to the strap 2112 and the locking geometry 620 such that there is positive engagement between the tooth 624 and the notches 3310 to bias the locking mechanism toward the locked position. The arm 622 (and other arms described herein) can be substantially rigid but can flex about a point of connection between the arm 622 and the first strap 2112.

Figure 18A:
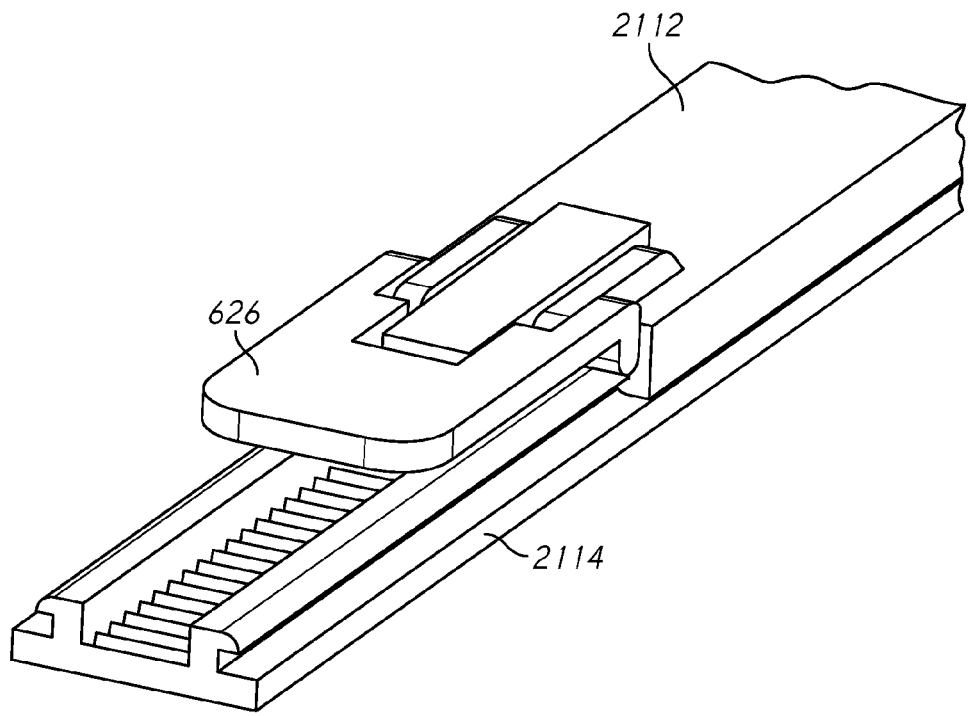
FIGS. 18A-18C are perspective, longitudinal cross-sectional, and enlarged longitudinal cross-sectional views, respectively, of a variation of the adjustment arrangement of FIGS. 4A and 4B including an example embodiment of a locking mechanism in a locked position.
Figure 18B:
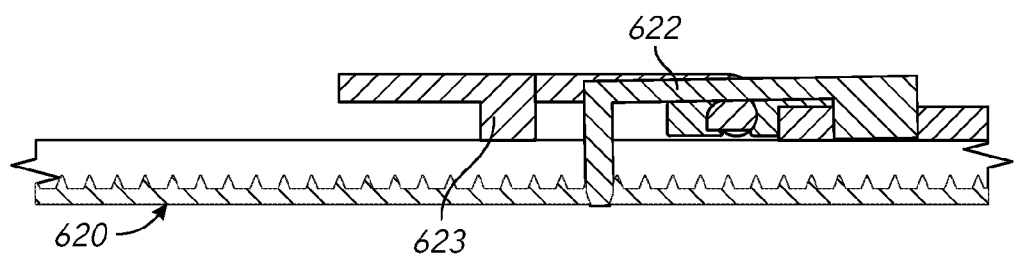
Figure 18C:
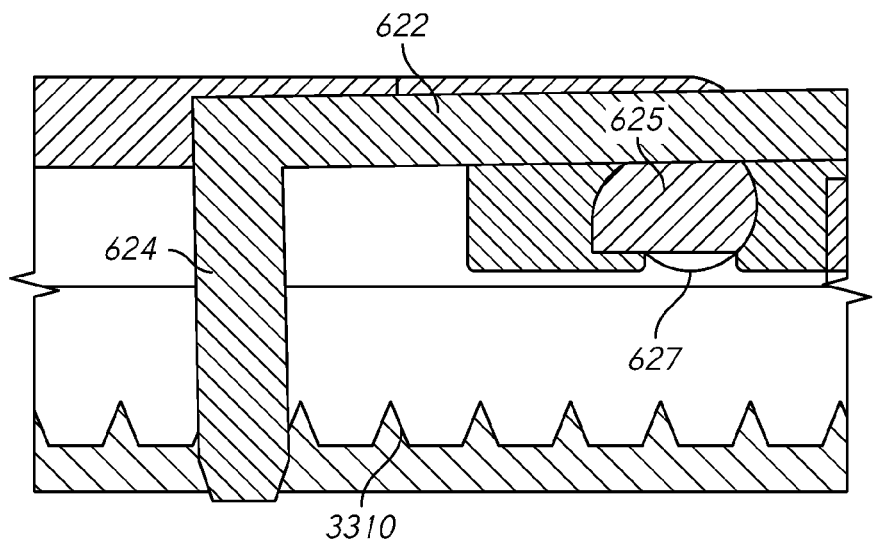
Figure 18D:
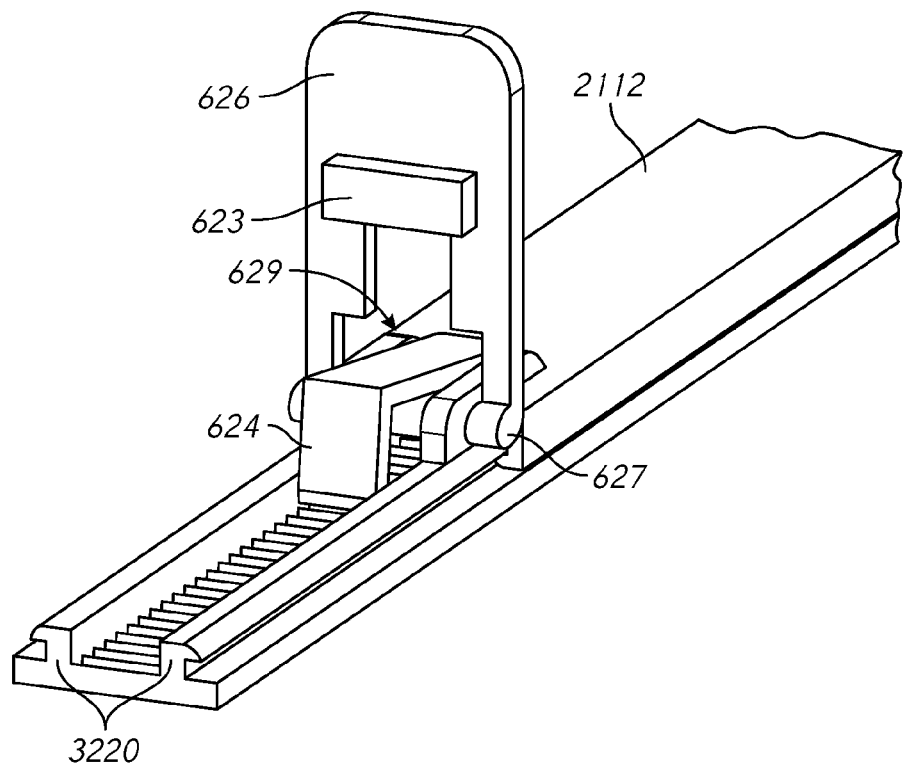
FIGS. 18D-18F are perspective, longitudinal cross-sectional, and enlarged longitudinal cross-sectional views, respectively, of the locking mechanism of FIGS. 18A-18C in an unlocked position.
Figure 18E:
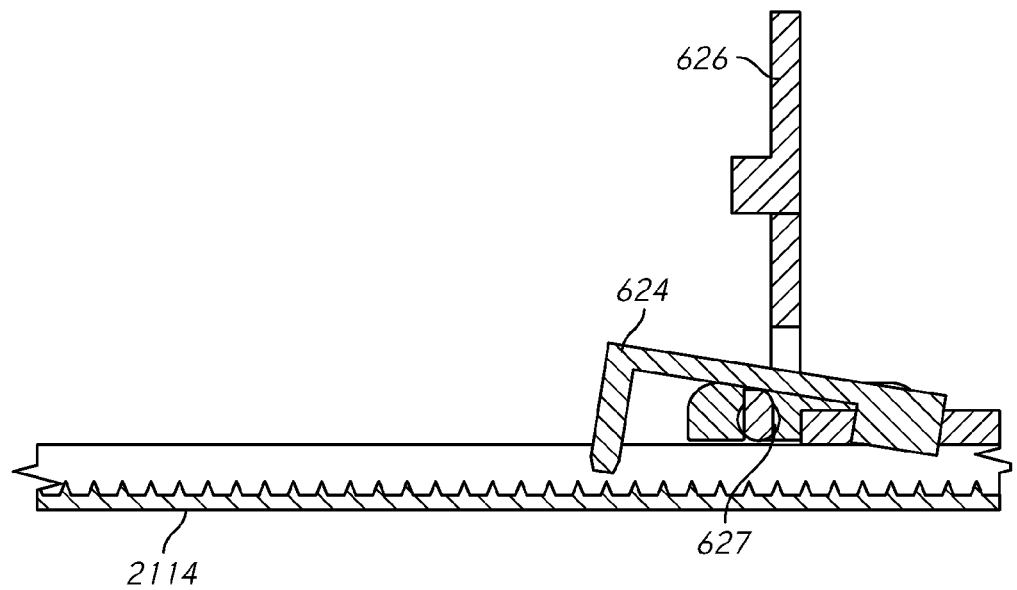
Figure 18F:
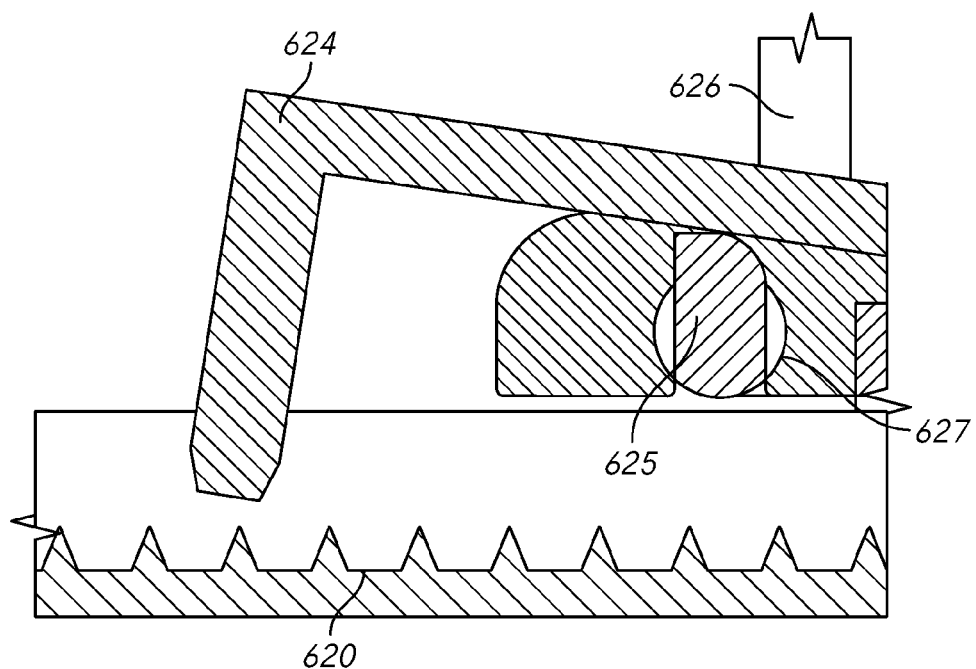

In this embodiment, the locking mechanism includes a pull tab 626 that includes an axle 627. The axle 627 can have a cam 625 on or near a mid-section of the axle 627. In some embodiments, the axle 627 is secured to the first strap 2112 by an integrally formed snap-fit clip that extends from the strap 2112 on either side of the tooth 624. The pull tab 626 can include an aperture 629 that accommodates the tooth 624 and allows the tooth 624 to pass through to the locking geometry 620. The aperture 629 accommodating the tooth 624 can allow the pull tab 626 to lie generally flat and parallel to the straps 2112, 2114 when in the locked position. An underside of the pull tab 626 (i.e., a side or surface of the pull tab 626 that faces the first strap 2112) can include a retaining post 623. The retaining post 623 fits tightly between the rails 3220 of the second strap 2114 when the pull tab 626 is in the locked position such that friction between the retaining post 623 and the rails 3220 retains or secures the pull tab 626 in the locked position until the user applies sufficient force to overcome the friction and lift the pull tab 626 to an unlocked position, which is shown in FIGS. 18D-18F.

When the user pulls on the pull tab 626 in the unlocked position, the pull tab 626 rotates the axle 627, which in turn rotates the cam 625, which lifts the arm 622 and disengages the tooth 624 from the notches 3310. The straps 2112, 2114 can then be moved relative to each other to adjust the strap length. Pulling on the pull tab 626 to adjust the strap can be similar to a zipper and can be intuitive to the user such that the locking and unlocking functionality can be somewhat hidden. In some embodiments, pulling the pull tab 626 can cause the tooth 624 to completely disengage from the notches 3310 such that the straps 2112, 2114 can be moved relative to each other equally easily in either directly. In other embodiments, pulling the pull tab 626 can cause the tooth 624 to only partially disengage from the notches 3310 and can allow the tooth 624 to slide along the tops of the notches 3310 (for example, similar to the embodiment of FIG. 15A). In such an embodiment, the shape of the tooth 624 and the shape of the notches 3310 can be selected to resist movement of the straps 2112, 2114 relative to each other more in one direction than in the opposite direction.

FIGS. 19A-19D show example embodiments of a locking mechanism that includes a pull tab 726 and a tooth 724 that engages or contacts a locking geometry 720 that has the notches 3310. The tooth 724 and the notches 3310 can have various shapes as described herein with respect to other embodiments. In the embodiment of FIGS. 19A-19B, the tooth 724 is somewhat teardrop shaped. In the embodiment of FIGS. 19C-19D, the tooth 724 is somewhat wedge-shaped or triangular. In some embodiments, the tooth 724 is integrally formed with the pull tab 726. The tooth 724 can be made of the same or a different material as the pull tab 726. The tooth 724 can be made of a material such as TPU. In some embodiments, the tooth 724 is overmolded onto an underside of the pull tab 726. The pull tab 726 is pivotally connected to the first strap 2112 by a hinge 727. In some embodiments, an extension 726a of the pull tab 726 can be positioned in a recess defined between two outer projections 2112a of the strap 2112, such as in the embodiment shown in FIG. 19C, and a pin or axle can extend through the projections 2112a and extension 726a to allow the extension 726a and pull tab 726 to rotate or pivot relative to the projections 2112a and the first strap 2112. The tooth 724 is positioned proximate the hinge 727, for example, on an underside of the extension 726a in the configuration shown in FIG. 19D. The locking tooth 724 can form a cam along the hinge 727.

The pull tab 726 can include a pair of retaining posts 723, one extending downward from each side of the pull tab 726, which is shown in FIG. 19D. In some embodiments, the pull tab 726 includes only one retaining post 723 on one side of the pull tab 726. The retaining posts 723 include flanges 723a that extend perpendicular to the main body of the posts 723 and parallel to the pull tab 726. The retaining posts 723 clip around the sides or edges of the second strap 2114 such that the flanges 723a are on an outer surface of the second strap 2114 (i.e., a surface that faces away from the first strap 2112) to secure the pull tab 726 in a locked position, which is shown in FIGS. 19B and 19C. The retaining posts 723 can be integrally formed with the pull tab 726. The retaining posts 723 can be made of the same material or a different material as the pull tab 726. In some embodiments, the retaining posts 723 are overmolded onto the pull tab 726. To adjust the length of the strap, the user lifts the pull tab 726 away from the second strap 2114, releasing the retaining posts 723 from the second strap 2114 and rotating the tooth 724 away from the locking geometry 720 (as the tooth 724 rotates with the pull tab 726 about the hinge 727) to disengage the tooth 724 from the notches 3310. The straps 2112, 2114 can then be moved relative to each other. The locking mechanism of FIGS. 19A-19D can advantageously be low profile.

Figure 20C:
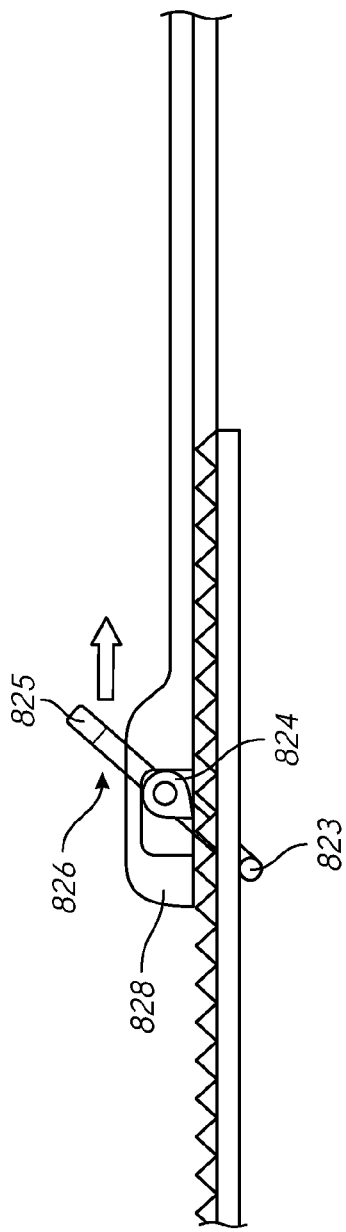
FIG. 20C is a longitudinal cross-sectional view of the locking mechanism of FIGS. 20A-20B in an unlocked position.
Figure 20D:
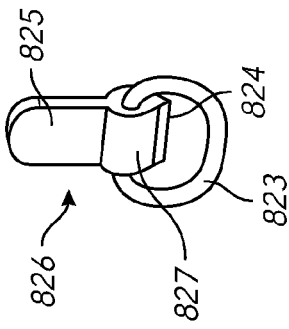
FIG. 20D is a perspective view of the pull tab portion of the locking mechanism of FIGS. 20A-20C.

FIGS. 20A-20E show an example embodiment of a locking mechanism that includes a pull tab 826, a pull tab retainer 828, and a tooth 824 that engages or contacts a locking geometry 820 that includes the notches 3310. The tooth 824 and the notches 3310 can have various shapes as described herein with respect to other embodiments. The pull tab 826 includes an o-ring 825, a grip portion 825, a pivot 827, and the tooth 824, which is shown in FIG. 20D. The grip portion 825, the pivot 827, and/or the tooth 824 can be integrally formed and can be formed from the same material. Alternatively, the tooth 824 can be formed of a different material from the pivot 827 and/or the grip portion 825 and can be coupled to the pivot 827, for example, via overmolding. The pivot 827 can be generally cylindrical. The grip portion 825 can extend from the pivot 827 such that the length of the grip portion 825 is perpendicular to the pivot 827 and the tooth 824 can extend from the pivot 827 generally opposite from the grip portion 825. The grip portion 825 and/or tooth 824 can extend along a length of the pivot 827. The o-ring 823 can be elastic. The o-ring 823 extends through a center of the pivot 827 and around the second strap 2114 to secure the pull tab 826 to the second strap 2114. The tooth 824 can be biased toward a locked positon as shown in FIG. 20A, for example, by the o-ring 823.

Figure 20E:
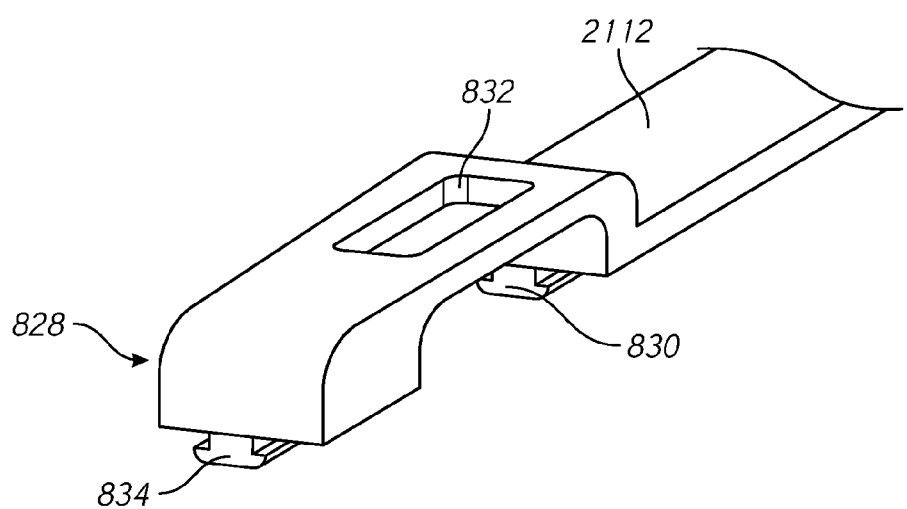
FIG. 20E is a perspective view of the pull tab retainer portion of the locking mechanism of FIGS. 20A-20C.

The pull tab retainer 828, shown in FIG. 20E and shown coupled to the pull tab 826 in FIG. 20B, can be integrally formed with or can be coupled to the free end of the first strap 2112. The pull tab retainer 828 has an arch 830 that sits or extends over the pivot 827 and allows the pivot 827 to move below the arch 830 and an aperture 832 that allows the grip portion 825 to extend through the pull tab retainer 828. The arch 830 is high enough to provide clearance for the tooth 824 to be fully disengaged from the notches 3310 in an unlocked position. The retainer 828 can be secured to the second strap 2114 in the locked position by one or more rails 834, which is shown in FIG. 20E. The rails 834 can clip between and provide friction with the inner rails 3220 of the second strap 2114.

To adjust the length of the strap, the user can grip and pull the grip portion 825 of the pull tab 826 away from the second strap 2114, which can stretch the o-ring 823 to allow the tooth 824 to be disengaged from the notches 3310 as shown in FIG. 20C so that the straps 2112, 2114 can be moved relative to each other. The user can pull on the grip portion 825 such that the grip portion 825 contacts the perimeter or edge, either at the edge closest to the strap 2112 or away from the strap 2112, of the aperture 832 of the pull tab retainer 828 to cause the retainer 828, and therefore the strap 2112, to move in one direction or another to lengthen or shorten the strap length.

FIGS. 21A-21D show an example embodiment of a locking mechanism including a sliding lock 928 and a tooth 924 that engages or contacts a locking geometry 920 having the notches 3310. The tooth 924 and the notches 3310 can have various shapes as described herein with respect to other embodiments. The tooth 924 is disposed at or near the free end of the first strap 2112 and protrudes toward the second strap 2114. The sliding lock 928 can have a substantially rectangular, C-shaped, squared C-shaped, or other suitable cross-sectional profile. The sliding lock 928 has a top wall and two side walls extending perpendicularly from the top wall on either side of the top wall. The top wall is disposed adjacent the outer surface of the first strap 2112, and the side walls can extend alongside the edges of the first and second straps 2112, 2114. The side walls can include rails that interlock with the rails 3220 of the second strap 2114 to secure the first strap 2112 to the second strap 2114.

Figure 21C:
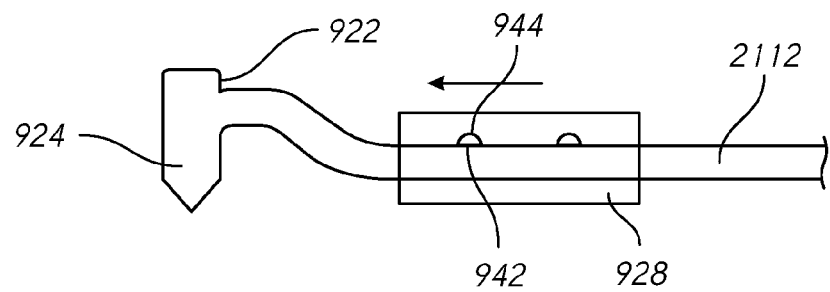
FIG. 21C is a partial longitudinal cross-sectional view of a variation of the locking mechanism of FIGS. 21A-21B in an unlocked position.
Figure 21D:
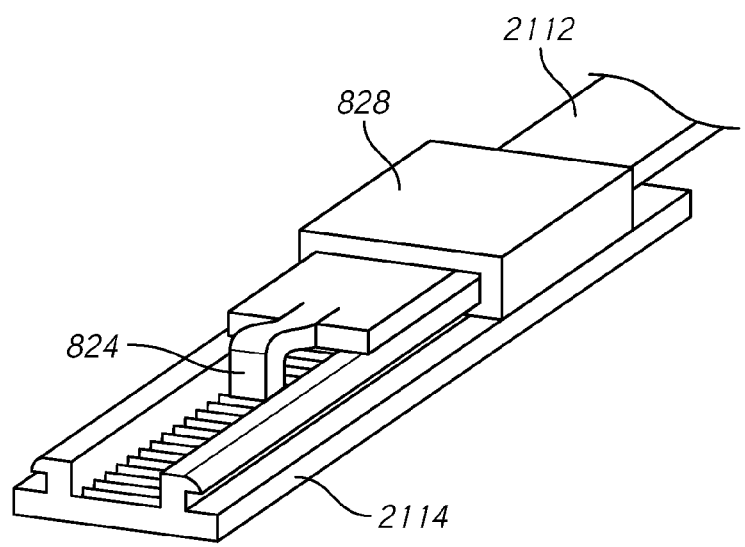
FIG. 21D is a perspective view of the locking mechanism of FIG. 21A.

The first strap 2112 can include a retaining bump 942 protruding from the outer surface of the first strap 2112 (i.e., the surface of the first strap 2112 facing away from the second strap 2114). An inner surface of the top wall of the sliding lock 928 can include a pair of retaining notches 944 that are parallel to and spaced apart along a length of the sliding lock 928. The retaining bump 942 engages the retaining notch 944 farther away from the tooth 924 in a locked position, as shown in FIG. 21B, and engages the retaining notch 944 closer to the tooth 924 in an unlocked position, as shown in FIG. 21A. In the locked position, the sliding lock 928 is closer to the free end of the first strap 2112 and the tooth 924 (e.g., adjacent the tooth 924) and holds the tooth 924 down into engagement with the notches 3310. In the unlocked position, the sliding lock 928 is farther away from the free end of the first strap 2112 and the tooth 924 such that a greater length of the first strap 2112 extends beyond the sliding lock 928, thereby allowing the free end of the first strap 2112 to move away from the second strap 2114 and the tooth 924 to disengage from the notches 3310. The sliding lock 928 can also be in an unlocked position when the retaining bump 942 is not engaged with either of the retaining notches 944. To adjust the length of the strap, the user slides the sliding lock 938 away from the tooth 924 until the retaining bump 942 engages the retaining notch 944 closer to the tooth 924. To lock the length of the strap, the user slides the sliding lock 928 toward the tooth 924 until the retaining bump 942 engages the retaining notch 944 farther away from the tooth 924. The locking mechanism of FIGS. 21A-21D can advantageously have a low profile.

In some embodiments, the free end of the first strap 2112 includes a hard stop 922 extending from the first strap 2112 in a direction opposite that of the tooth 924, as shown in FIG. 21C. The hard stop 922 can prevent or inhibit the sliding lock 928 from sliding off of the free end of the first strap 2112.

FIGS. 22A-22B illustrate an example embodiment of a locking mechanism including a rotating gear 1022 and a flexible pawl 1024 that engages or contacts a locking geometry 1020 having a corresponding gear profile 1010 instead of the notches 3310. The flexible pawl 1024 extends from the free end of the first strap 2112 parallel to the length of the strap 2112. The flexible pawl 1024 can be made of a flexible material that is the same as or different than the material of the strap 2112. The flexible pawl 1024 can be integrally formed with or overmolded onto the strap 2112. The flexible pawl 1024 contacts the gear 1022 and resists movement of the gear 1022. A gear housing 1026 secures the gear 1022 to the first strap 2112. In some embodiments, the gear housing 1026 is formed by extensions extending from the sides or edges of the free end of the first strap 2112. The gear housing 1026 is positioned beyond (farther away from the strap 2112) the pawl 1024 such that the gear 1022 is located at a distance from the pawl 1024 to allow the pawl 1024 to contact or engage with the teeth 1028 of the gear 1022. The teeth 1028 of the gear 1022 correspond to and engage with the gear profile 1010 of the second strap 2114 and the pawl 1024.

To adjust the length of the strap, the user rolls the gear 1022 in either direction along the second strap 2114. The pawl 1024 flexes up or down to allow the gear 1022 to rotate in either direction (i.e., toward or away from the first strap 2112). Rotating the gear 1022 clockwise (in the configuration and view of FIGS. 22A-22B) causes the pawl 1024 to flex down toward the second strap 2114 due to contact between the pawl 1024 and each of the teeth 1028 of the gear 1022. Once a tooth 1028 of the gear 1022 has passed the tip of the pawl 1024, the pawl 1024 springs, snaps or reverts to its neutral position generally parallel to the first strap 2112. Rotating the gear 1022 clockwise pushes the first strap 2112 away from the second strap 2114 to increase the length of the strap 2110. Rotating the gear counterclockwise (in the configuration of FIGS. 22A-22B) pulls the first strap 2112 toward the second strap 2114 to reduce the length of the strap 2110. The locking mechanism of FIGS. 22A-22B can provide the user with haptic or tactile feedback of each incremental adjustment so that the user can judge the degree to which the strap length is being changed. This locking mechanism also allows for small adjustments to be made more easily and/or in a more controlled manner.

Figure 23B:
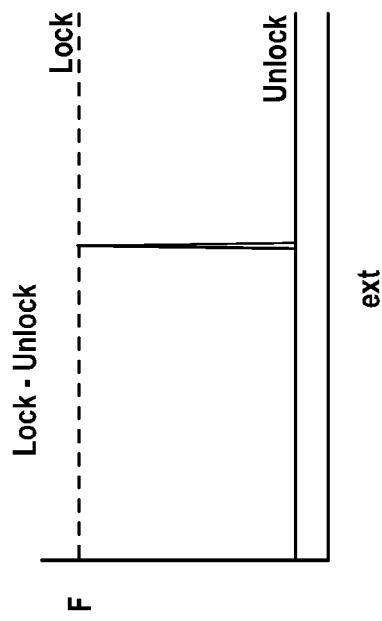
FIGS. 23A-23B show force extension profiles for various embodiments of locking mechanisms.
Figure 23A:
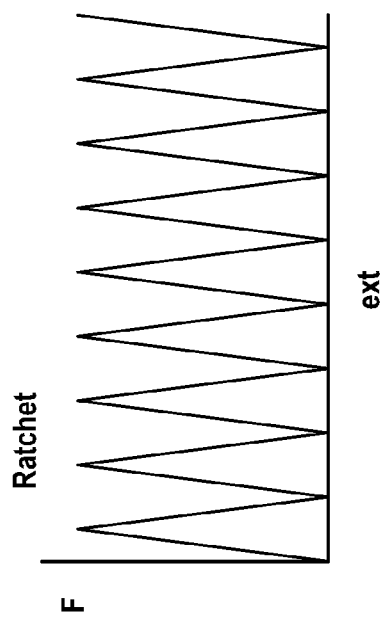

FIGS. 23A-23B illustrate force extension profiles for the locking mechanism shown in FIGS. 15A-22B. The "ratchet" force extension profile of FIG. 23A applies to the locking mechanisms of FIGS. 15A, 15C, 15D, 16A-16B, and 22A-22B. The "lock-unlock" force extension profile of FIG. 23B applies to the locking mechanisms of FIGS. 16A-16B, 17A-17C, 18A-18F, 19A-19D, 20A-20E, and 21A-21D. In the locking mechanisms that have a ratchet force extension profile, the force increases as the straps 2112, 2114 are extended relative to each other until the tooth (324, 424, 1028) passes over a notch 3310 or the gear profile 1010 feature. The force fluctuates as the tooth passes over multiple notches or gear profile features. In the locking mechanisms that have a lock-unlock force extension profile, the force required to extend the straps 2112, 2114 relative to each other is relatively low when the locking mechanism is in an unlocked position. The extension force increases dramatically, such that elongation of the straps 2112, 2114 relative to each other is inhibited or substantially prevented, when the locking mechanism is in a locked position.

Figure 11A:
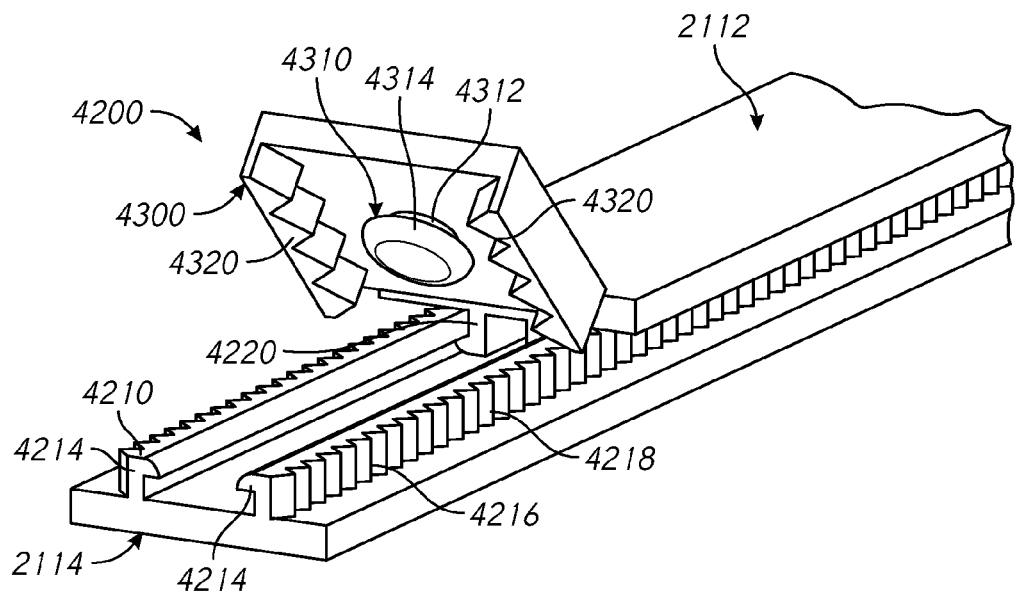
FIGS. 11A and 11B show perspective views of a variation of the adjustment arrangement of FIGS. 5A and 5B, including a lock, in both an open position and a locked position.
Figure 11B:
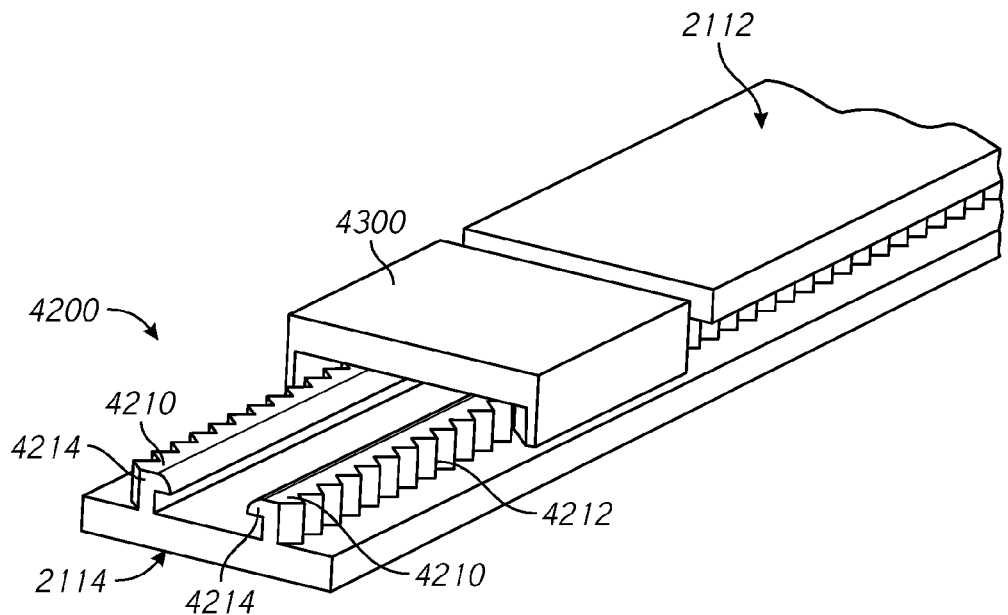

FIGS. 11a to 11c show a variation of the adjustment arrangement 4200 (shown in FIGS. 5A and 5B), which variation comprises a lock 4300. The outer rails 4210 include locking geometry 4216 that is configured to engage with the lock 4300 to prevent or inhibit the first and second straps 2112, 2114 from sliding relative to each other. Preventing or inhibiting the sliding of first strap 2112 relative to the second strap 2114 allows a user-defined size of the headgear assembly 2100 to be maintained more reliably.

The locking geometry 4216 comprises a plurality of triangular notches 4218. The notches 4218 are positioned on the outer sides of the outer rails 4210 and extend perpendicular to second strap 2114 towards first strap 2112. The notches 4218 are configured to engage with a corresponding feature of the lock 4300. In alternative embodiments, there may be notches only on one of the outer rails.

The lock 4300 is a rectangular button that is pivotally attached to an end of the first strap 2112 (i.e., a free end of the first strap 2112 opposite the junction 2125) such that the lock 5300 can be moved between an open position (as shown in FIG. 11A) and a locked position (as shown in FIG. 11B). The lock 4300 comprises a retaining feature 4310 and two sets of locking notches 4320. The retaining feature 4310 comprises a post 4312, which is cylindrical in the illustrated embodiment, having a mushroom head 4314. Cylindrical post 4312 protrudes from an inner surface of the lock 4300. The mushroom head 4314 is configured to engage with the flanges 4214 of the outer rails 4210 such that the lock 4300 can be secured in a locked position. For example, if the mushroom head 4314 is pushed toward and into engagement with the flanges 4214, a sufficient force on the lock 4300, and therefore on the mushroom head 4314, can cause the flanges 4214 to deflect outwardly such that the mushroom head 4314 can move into a space between the flanges 4214 and the inner surface 2118 of the second strap 2114. The flanges 4214 can then return to their normal position substantially perpendicular to the inner surface 2118 of the second strap 2114 to secure the mushroom head 4314, and therefore the lock 4300, to the second strap 2114. In a locked position, the lock 4300 is substantially parallel to the first and second straps 2112, 2114.

The locking notches 4320 comprise a plurality of triangular projections that are joined together, side by side, and that extend along at least a portion of the length of the two opposing edges of the lock 4300. The locking notches 4320 match or correspond to the geometry of the notches 4218. The locking notches 4320 are positioned such that the triangular projections point towards the retaining feature 4310 and are configured to engage and mesh or match with the notches 4218 when the lock 4300 is in a locked position.

In other embodiments, the notches 4218 may have any appropriate shape that prevents or inhibits longitudinal movement and/or sliding of the first and second straps 2112, 2114 relative to each other. This may include, but is not limited to, square or rectangular teeth/notches or asymmetric teeth/notches.

A non-limiting variation of the lock 4300 is shown in FIG. 11C. In this variation, the first strap 2112 includes a fabric layer 4330 on its outer surface. The fabric layer 4330 extends along the length of the first strap 2112, beyond the free end of the first strap 2112, and onto the outer surface of the lock 4300. The fabric layer 4330 can be permanently joined to the strap 2112 and the lock 4300 by adhesive, welding, or over-molding, for example but without limitation.

The fabric layer 4330 forms a flexible joint or hinge 4332 between the first strap 2112 and the lock 4300. The hinge 4332 allows the lock 4300 to pivot about the end of the first strap 2112 such that the lock 4300 can be moved between an open position and a locked position. The fabric layer 4330 may extend beyond the end of the lock 4300 to form a pull tab 4334. The pull tab 4334 is configured to provide a feature that can be gripped by a user and pulled on to release the lock 4300 from the locked position.

Figure 12:
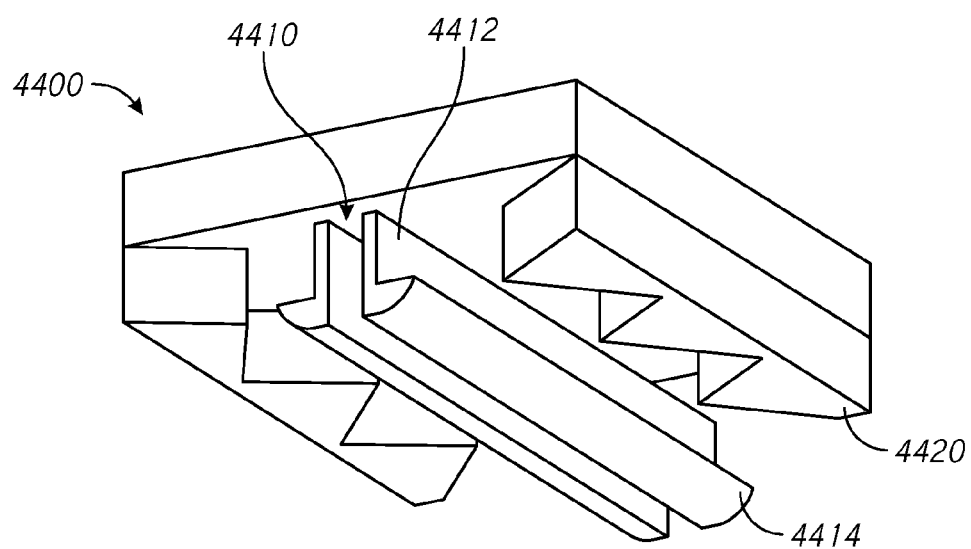
FIG. 12 is a perspective view of another embodiment of the lock of FIGS. 11A and 11B.

FIG. 12 shows another non-limiting embodiment of a lock 4400, which can be similar to the lock 4300 described above in some ways. The lock 4400 is configured to engage with the locking geometry 4216 (of the embodiment shown in FIGS. 11A and 11A) and to secure the position of the first strap 2112 relative to the second strap 2114.

The lock 4400 is a rectangular button that may be pivotally attached to the free end of the first strap 2112 such that it can be moved between an open position and a locked position. The lock 4400 comprises a retaining feature 4410 and two sets of locking notches 4420. The retaining feature 4410 comprises a pair of locking rails 4412, which can be similar to the inner rails 4220 described above, each having a flange 4414. The flanges 4414 are configured to engage with the flanges 4214 of the outer rails 4210 such that the lock 4400 can be secured in a locked position.

The locking notches 4420 can be configured in the same way as the locking notches 4320 described above and can comprise a plurality of triangular projections that are joined together, side by side, and that extend along at least a portion of the length of two opposing edges of the lock 4400. The locking notches 4420 match or correspond to the geometry of the notches 4218 described above. The locking notches 4420 are positioned such that the triangular projections point towards the retaining feature 4410 and the locking notches 4420 are configured to engage and mesh or match with the notches 4218 when the lock 4400 is in a locked position, in use.

FIGS. 13A and 13B show another non-limiting exemplary embodiment of an adjustment arrangement 6200 comprising a first strap 2112 and a second strap 2114 configured for use in combination with the headgear assembly 2100. The first strap 2112 comprises an inner rail 6220 (shown in FIG. 13b). The inner rail 6220 can be the same or similar to the inner rail 5220 which has been previously described herein. In alternative embodiments, the first strap 2112 may include more than one inner rail, such as but not limited to, the inner rails 3220, 4220, as previously described herein. The second strap 2114 comprises a pair of outer rails 6210, which can include the locking geometry 6216. The locking geometry can include a plurality of triangular notches 6218 that are substantially similar to the notches 4218 of the embodiment of FIGS. 11A to 11C. The outer and inner rails 6210, 6220 can be configured to secure the first and second straps 2112, 2114 together such that they can slide freely relative to each other with minimal friction. This may improve ease of adjustment for a user.

The adjustment arrangement 6200 further comprises a first lock 6300 and a second lock 6400. The first and second locks 6300, 6400 can provide differing functionality to the adjustment arrangement 6200. In this embodiment, the first lock 6300 locks the position of the first and second straps 2212, 2214 relative to each other such that the size of the headgear can be adjusted by a user. The second lock 6400 provides a source of friction between the first and second straps 2112, 2114 such that the straps 2112, 2114 may not unintentionally slide relative to each other when the first lock 6300 is in an open position (as shown in FIG. 13A).

The first lock 6300 can be configured to be similar to the locks 4300, 4400 of the embodiments of FIGS. 11A-11C and FIG. 12 and forms a hinged extension to the first strap 2112. The first lock 6300 comprises a retaining feature (not shown) that is configured to secure the lock 6300 in a locked position and a plurality of locking notches (not shown) that are configured to prevent or reduce the likelihood of the first and second straps 2112, 2114 sliding relative to each other.

The second lock 6400 forms a hinged extension of the second strap 2114 and comprises a pair of outer rails 6410. The outer rails 6410 can be configured similar to the outer rails 6210 but with larger dimensions such that there is greater interference between the outer rails 6410 and the inner rail 6220 when the lock is in a locked position (as shown in FIG. 13A). This increased interference provides a constant friction force between the first and second straps 2112, 2114, which allows their positioning relative to each other to be maintained whilst tension forces between the straps 2112, 2114 remain below the force required to overcome the friction. This may prevent or inhibit unintentional adjustment of the headgear size when the first lock 6300 is in an open position.

An advantage of the headgear assembly 2100 of the present disclosure is that the thickness of the straps is less than traditional Breathoprene® headgear assemblies. This is a result of the plastic top and rear straps 2110 and 2120 being more rigid and providing greater structure for a thinner cross-section. The interlocking structure of the outer and inner rails 3210, 4210, 3220, 4220 reduces the thickness of the top strap 2110 where the first and second straps 2112, 2114 overlap, that is, the headgear has a thickness that is less than twice the thickness of a single strap. This reduced thickness makes the headgear assembly 2100 lower profile and less bulky, which may improve user comfort.

FIGS. 14A-14B illustrate another example embodiment of a locking mechanism that can be used with a headgear assembly such as headgear assembly 2100. The first strap 2112 and the second strap 2114 can include rails such as those described in other embodiments herein. A free end of the first strap 2112 includes a first interlocking mechanism 102 that couples to the second strap 2114 and a free end of the second strap 2114 includes a second interlocking mechanism 104 that couples to the first strap 2112. In the illustrated embodiment, the first interlocking mechanism 102 comprises a loop or portion that encircles the second strap 2114. The second interlocking mechanism 104 comprises a loop or portion that encircles the first strap 2112. The first and second interlocking mechanisms 102, 104 can slide along the second and first straps 2114, 2112, respectively, to adjust a length of the strap 2110 and the size of the headgear assembly 2100. A friction force can be generated between the first interlocking mechanism 102 and the second strap 2114 and between the second interlocking mechanism 104 and the first strap 2112 such that the interlocking mechanisms 102, 104 cannot slide freely along the straps 2114, 2112 but can slide along the straps 2114, 2112 when the friction force is overcome, for example, by the user applying a sufficient force to overcome the friction force. The friction force can provide the user with tactile feedback during adjustment.

In some embodiments, the interlocking mechanisms 102, 104 have different functions or serve different purposes. For example, one of the interlocking mechanisms 102, 104 can lock the straps 2112, 2114 relative to each other when desired, for example, in a user-defined length or position relative to each other. The other of the interlocking mechanisms 102, 104 can provide a friction force between the straps 2112, 2114 so that movement between the straps 2112, 2114 is controlled rather than completely free even when the interlocking mechanism 102, 104 that provides a lock is in an unlocked position. In some embodiments, the interlocking mechanisms 102, 104 can provide different functionality in different directions (e.g., may allow adjustment more easily in one direction, such as shortening the length of the strap, and restrict adjustment in the opposite direction, such as lengthening the strap). In other embodiments, the interlocking mechanisms 102, 104 can provide a cumulative effect (e.g., may both contribute to resisting movement in either direction).

The first and second interlocking mechanisms 102, 104 can be integrally formed with or coupled to the first and second straps 2112, 2114, respectively. The interlocking mechanisms 102, 104 can couple to the straps 2114, 2112, respectively, permanently or removably or temporarily.

The locking mechanism of FIGS. 14A-14B can advantageously prevent, inhibit, or reduce the likelihood of flapping or tangling of the straps 2112, 2114. This locking mechanism can reduce tangling between the user's hair and the straps 2112, 2114.

FIGS. 24A-24C illustrate another example embodiment of an adjustment mechanism that can be used with a headgear assembly such as the headgear assembly 2100. One of the first and second straps 2112, 2114 includes a hollow outer tube 1302 and the other of the first and second straps 2112, 2114 includes an inner tube or inner member 1304. An o-ring 1306 is disposed about the inner member 1304 proximate the free end of the inner member 1304. As shown in FIG. 24B, the inner member 1304 can include a channel or groove 1308 extending around the circumference or outer surface of the inner member 1304, and the o-ring 1306 can be seated or disposed in the channel or groove 1308. In some configurations, the outer tube 1302 can include a channel or groove and the o-ring can be positioned within the channel or groove instead of being positioned in the channel or groove 1308 of the inner member 1304. An outer diameter of the inner member 1304 is smaller or less than an inner diameter of the outer tube 1302.

In use, a portion of the inner member 1304 including the free end of the inner member 1304 and the o-ring 1306 are disposed within the outer tube 1302 as shown in FIG. 24B. An outer diameter of the o-ring 1306 is sized such that the o-ring 1306 contacts and exerts radial forces on an inner wall of the outer tube 1302. Interference between the o-ring 1306 and the inner wall of the outer tube 1302 creates friction, which resists relative movement between the inner member 1304 and outer tube 1302 in both directions. The friction between the o-ring 1306 and the inner wall of the outer tube 1302 helps maintain the inner member 1304 at a particular position within the outer tube 1302 to help maintain a desired size of the headgear assembly. To adjust the headgear assembly, the user pushes the outer tube 1302 and inner member 1304 toward each other (to tighten the headgear) or pulls the outer tube 1302 and inner member 1304 away from each other (to loosen the headgear) with sufficient force to overcome the friction between the o-ring(s) 1306 and the inner wall of the outer tube 1302.

In some embodiments, for example as shown in FIG. 24C, a series of o-rings 1306 can be used to create the friction force between the outer tube 1302 and the inner member 1304. In the illustrated configuration, the series of o-rings 1306 are disposed about the inner member 1304. Three o-rings 1306 are shown in the embodiment of FIG. 24C, but more or fewer o-rings 1306 are also possible. The number of o-rings 1306 included can be chosen to achieve a particular desired or required level of friction. A greater number of o-rings 1306 can create a greater amount of friction.

FIGS. 25A-25E illustrate another example embodiment of an adjustment mechanism that can be used with a headgear assembly such as the headgear assembly 2100 described below. One of the first and second straps 2112, 2114 includes a hollow outer rail 1322 and the other of the first and second straps 2112, 2114 includes an inner or male rail 1324. Outer dimensions (i.e., length and width) of the inner rail 1324 are smaller or less than inner dimensions of the outer rail 1322. In use, a portion of the inner rail 1324 including the free end of the inner rail 1324 is disposed within the outer rail 1322 as shown in FIG. 25A.

An orifice or ring 1326 is coupled, removably or permanently, to or integrally formed with the free end of the outer rail 1322 and disposed about the inner rail 1324. In some embodiments, the ring 1326 is flexible. In some embodiments, the ring 1326 is made of or includes, for example, TPU (thermoplastic polyurethane) and/or rubber. The ring 1326 can be sized and/or constructed such that the ring 1326 contacts and constricts around the inner rail 1324. Interference between the inner rail 1324 and the inner wall of the ring 1326 can create friction, which resists relative movement between the inner rail 1324 and outer rail 1322. The friction between the inner rail 1324 and the inner wall of the ring 1326 helps maintain the inner rail 1324 at a particular position within the outer rail 1322 to help maintain a desired size of the headgear assembly. To adjust the headgear assembly, the user pushes the outer rail 1322 and inner rail 1324 toward each other (to tighten the headgear) or pulls the outer rail 1322 and inner rail 1324 away from each other (to loosen the headgear) with sufficient force to overcome the friction between the inner rail 1324 and the inner wall of the ring 1326.

In some embodiments, for example as shown in the sectional views of FIGS. 25C and 25D, one or a series of fins 1328 can be disposed along one or more inner surfaces of the ring 1326. In the illustrated embodiment, the fins 1328 are integrally formed with the ring 1326. In other embodiments, the fins 1328 can be formed separately from the ring 1326 and attached, removably or permanently, to the ring 1326. The fins 1328 are sized and formed to contact the inner rail 1324. Interference between the inner rail 1324 and the fins 1328 can create, or help create, the friction that resists relative movement between the inner rail 1324 and outer rail 1322. Four fins 1328 are shown in the embodiment of FIGS. 25C and 25D, but more or fewer fins 1328 are also possible.

The number and/or shape of the fins 1328 can be chosen to achieve a particular desired or required force profile or level of friction. A greater number of fins 1328 can create a greater amount of friction. In some embodiments, the fin(s) 1328 can be shaped to resist relative movement between the inner rail 1324 and outer rail 1322 equally in both directions (to resist tightening and loosening of the headgear relatively equally). In other embodiments, the fin(s) 1328 can be shaped to provide greater resistance to movement between the inner rail 1324 and outer rail 1322 in one direction and provide lesser resistance to movement and allow easier movement between the inner rail 1324 and the outer rail 1322 in the other direction. For example, the fin(s) 1328 can be shaped to allow for easier tightening of the headgear and provide greater resistance to loosening of the headgear.

Figure 25H:
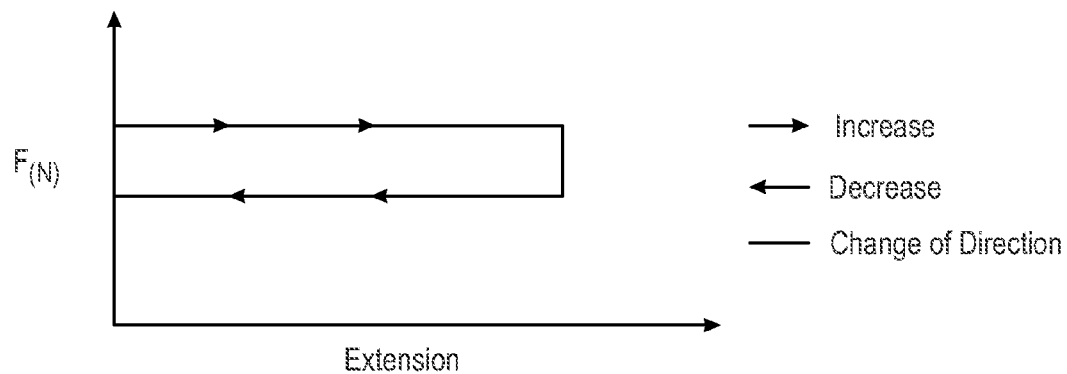
FIG. 25H shows a force profile for the fin of FIG. 25G.
Figure 25G:
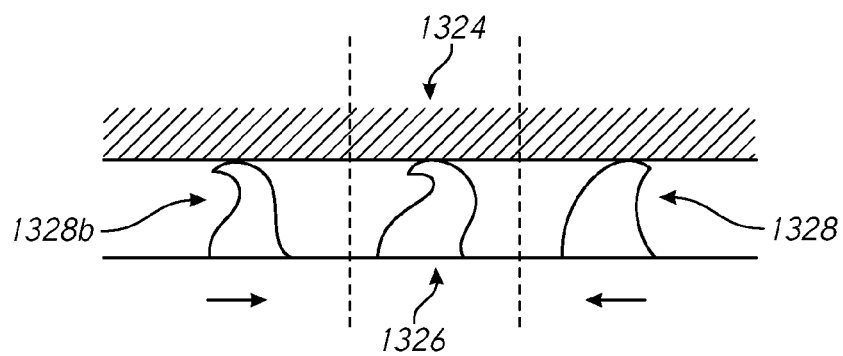
FIG. 25G shows the shape of one fin during adjustment.

FIG. 25E illustrates three example cross-sectional shapes for the fins 1328. The fin 1328a can be triangular and symmetrical as shown in FIG. 25E. The fin 1328c can be rounded or domed and symmetrical as shown in FIG. 25E. In use, the fins 1328a and 1328c resist relative movement between the inner rail 1324 and outer rail 1322 equally or substantially equally in both directions. In use, during adjustment, the point or peak bends towards the direction of movement of the inner rail 1324 (or away from the direction of movement of the outer rail 1322). If the user changes the direction of adjustment, the fin 1328a changes shape, or the peak bends in the opposite direction. In some embodiments, the point or peak may compress instead of or in addition to bending to allow for movement between the inner rail 1324 and the outer rail 1322. FIG. 25F illustrates a force profile for the fin 1328a. The fin 1328c may exhibit the same or a similar force profile. As shown, the friction force remains constant or relatively constant as the headgear continues to be adjusted in a particular direction (i.e., tightening or loosening). However, the friction force increases when the user changes the direction of adjustment as the peak of the fin 1328a turns toward the opposite direction. This increase in friction force can be a momentary or temporary change as the deformation of the fin 1328a is overcome and/or reversed as the user changes the direction of adjustment. The friction force then returns to the same or approximately the same level as during adjustment in the original or previous direction. In some embodiments, such a force profile allows the headgear to be more easily adjusted once the user overcomes the initial friction force required to initiate movement or adjustment of the inner rail 1324 and the outer rail 1322 and then provides greater initial resistance against movement or adjustment in the opposite direction. In some embodiments, the fins 1328a are sized such that the user may not be aware of the temporary increase in friction force when changing the direction of adjustment. The fin 1328b can be asymmetrical as shown. In use, the fin 1328b provides greater resistance to movement between the inner rail 1324 and the outer rail 1322 in one direction compared to the other, opposite direction. For example, the fin 1328b can be shaped or oriented to provide greater resistance to lengthening the strap as illustrated in FIG. 25G and the force profile of FIG. 25H. As shown to the right of FIG. 25G, the fin 1328b assumes its molded, default, or resting state or shape when the inner rail 1324 moves into the outer rail 1322 to shorten the strap. To move the inner rail 1324 away from the outer rail 1322 to lengthen the strap, the tip of the fin 1328b is dragged or pulled toward the opposite direction as shown to the left of FIG. 25G. The fin's 1328b bias toward its molded or default state increases the resistance and friction force during extension of the strap, as shown in the force profile of FIG. 25H. As shown in FIG. 25G, a contact surface between the fin 1328b and the inner rail 1324 is also larger during extension, which can contribute to the increased friction force and resistance to extension.

FIGS. 26A-26C illustrate another example embodiment of an adjustment and/or locking mechanism that can be used with a headgear assembly such as the headgear assembly 2100. The adjustment mechanism includes rollers 1336. The rollers 1336 can be balls, cylinders, or the like. As shown, a roller 1336 is disposed on or adjacent the top (or a first side) of one of the first and second straps 2112, 2114 (illustrated as the second strap 2114 in FIGS. 26A-26C), and another roller 1336 is disposed on or adjacent the bottom (or an opposite side) of the first or second strap 2112, 2114 (second strap 2114 in the illustrated embodiment). A housing 1338 is disposed around the first or second strap 2112, 2114 (second strap 2114 in the illustrated embodiment), and the rollers 1336 are disposed within an internal cavity 1337 of the housing 1338. The other of the first and second straps 2112, 2114 (e.g., the first strap 2112 in the embodiment of FIGS. 26A-26C) can be coupled or attached to the housing 1338. As the user moves the straps 2112, 2114 relative to each other to adjust the headgear, the rollers 1336 can roll along the strap 2114 to allow for adjustment. Friction between the rollers 1336 and the strap 2114 can resist relative movement between the straps 2112, 2114, and therefore adjustment of the headgear, unless and until the user applies sufficient force to overcome the friction.

In the illustrated embodiment, an inner wall 1339 of the housing 1338, i.e., the wall surrounding and defining the cavity 1337, is tapered toward one end of the housing 1338 and the strap 2114 such that the cavity 1337 is larger toward one end of the housing 1338 and the strap 2114. In some embodiments, toward the smaller end of the cavity 1337, a distance between the strap 2114 and the inner wall 1339 decreases to a distance about the same as or less than a diameter of the rollers 1336. Toward the opposite, larger end of the cavity 1337, the distance between the strap 2114 and the inner wall 1339 can be greater than the diameter of the rollers 1336.

The tapered inner wall 1339 of the housing 1338 causes the friction created by interference between the rollers 1336 and strap 2114 to be directional. For example, in some embodiments, the housing 1338 and tapered inner wall 1339 can be oriented such that the adjustment mechanism allows for relatively easier tightening of the headgear but provides greater resistance against loosening the headgear. In other embodiments, the adjustment mechanism may allow relatively easier loosening of the headgear. As the user moves the strap 2114 toward the larger end of the cavity 1337 (i.e., toward the right in the embodiment illustrated in FIGS. 26A-26B) as indicated by the arrow in FIG. 26B and/or moves the housing 1338 toward the smaller end of the cavity 1337, the rollers 1336 move into or reside in the larger end of the cavity 1337 as shown and are able to rotate freely or relatively freely, which allows for adjustment in that direction. As the user moves the strap 2114 toward the smaller end of the cavity 1337 (toward the left in the illustrated embodiment) as indicated by the arrow in FIG. 26A and/or moves the housing 1338 toward the larger end of the cavity 1337, the rollers 1336 move into or reside in the smaller end of the cavity 1337. The smaller end of the cavity 1337 restricts rotation of the rollers 1336, thereby restricting adjustment in that direction. The rollers 1336 can become wedged between the inner wall 1339 and the strap 2114, and the resulting greater friction between the rollers 1336 and strap 2114 can prevent or inhibit adjustment in that direction.

FIGS. 27A-27B illustrate another example embodiment of an adjustment and/or locking mechanism that can be used with a headgear assembly such as the headgear assembly 2100. One of the first and second straps 2112, 2114 includes a spring-loaded arm 1346. In some configurations, the arm 1346 can be integrally formed with one of the first and second straps 2112, 2114. In the illustrated embodiment, the arm 1346 is coupled to or integrally formed with a housing 1348. In use, the arm 1346 extends at an angle from the housing 1348 or other portion of the strap and a friction surface at a free end of the arm 1346 contacts and applies a force against the other of the first and second straps 2112, 2114 (illustrated as the second strap 2114 in FIG. 27A). Friction created by the contact between the arm 1346 and the second strap 2114 can be directional such that it is easier to adjust the headgear in one direction than the other (e.g., easier to tighten than to loosen the headgear or vice versa). The angle of the arm 1346 and/or the shape of the friction surface can affect the friction force. FIG. 27D illustrates example shapes for the friction surface 1347. FIG. 27C illustrates example force profiles of the friction force created between the friction surface 1347 and the strap 2114. In some configurations, the end of the arm 1346 is captured between the housing 1348 and the strap.

FIGS. 28A-28D illustrate another example embodiment of an adjustment mechanism that can be used with a headgear assembly such as the headgear assembly 2100. One of the first and second straps 2112, 2114 includes a hollow outer tube 1352 and the other of the first and second straps 2112, 2114 includes an inner tube or core 1354. The outer tube 1352 can be made of rubber and/or TPU, which can advantageously allow the strap to feel comfortable to the user and provides a desired level of flexibility and resilience. Outer dimensions of the inner core 1354 are smaller or less than inner dimensions of the outer tube 1352 and, in use, at least a portion of the inner core 1354 is disposed within the outer tube 1352. The outer tube 1352 includes a lock tooth or protrusion 1356 extending from an inner wall of the outer tube 1352 into the hollow interior of the outer tube 1352. The lock tooth 1356 can be integrally formed with or attached to the inner wall of the outer tube 1352. In some configurations, the lock tooth 1356 can be integrally formed with the outer tube 1352 by indenting or otherwise offsetting a portion of the outer tube 1352 in an inwardly disposed direction. The inner core 1354 includes a series of depressions 1358. The depressions 1358 are sized, shaped, and positioned to receive at least a portion of the lock tooth 1356.

In a neutral position or state, the lock tooth 1356 is disposed or seated in one of the depressions 1358, as shown in FIG. 28C. This restricts relative movement between the outer tube 1352 and inner core 1354 and locks the adjustment mechanism and size of the headgear. As shown, the outer tube 1352 can have an elongated or flattened oval shape. The inner core 1354 can have a similar elongated or flattened oval shape. The lock tooth 1356 can be positioned along one of the longer sides of the oval shape. The outer tube 1352 and the inner core 1354 are sized such that in the neutral state, the lock tooth 1356 is disposed at least partially in one of the depressions 1358 and there is a gap between sides of the inner core 1354 and the inner wall of the outer tube 1352. To adjust the length of the strap, the user squeezes the sides of the outer tube 1352 as shown in FIG. 28A. This causes the outer tube 1352 to assume a relatively more circular shape. Squeezing the sides of the outer tube 1352 causes the look tooth 1356 to lift out of the depression 1358, as shown in FIG. 28D. When the sides of the outer tube 1352 are squeezed to lift the lock tooth 1356 out of the depression, the sides of the inner wall of the outer tube 1352 may contact the sides of the inner core 1354, as shown in FIG. 28D. With the sides of the outer tube 1352 squeezed and the lock tooth 1356 removed from the depression 1358, the user can telescope the inner core 1354 into or out of the outer tube 1352 to adjust the length of the strap. Once the user has achieved the desired strap length, he or she can release the squeeze on the outer tube 1352 so that the outer tube 1352 returns to a neutral position and, when the lock tooth 1356 is aligned with one of the depressions 1358, the lock tooth 1356 will seat in another of the depressions 1358. In this embodiment, the adjustment and locking mechanism is advantageously hidden.

FIGS. 29A-29C illustrate another example embodiment of an adjustment mechanism that can be used with a headgear assembly such as the headgear assembly 2100. One of the first and second straps 2112, 2114 includes a hollow outer sleeve 1362, and the other of the first and second straps 2112, 2114 includes an inner rail 1364. The outer sleeve 1362 includes a hollow locking button 1365. Outer dimensions of the inner rail 1364 and the locking button 1365 are smaller or less than inner dimensions of the outer sleeve 1362 and, in use, at least a portion of the inner rail 1364 is disposed within the button 1365 and outer sleeve 1362.

As shown, the locking button 1365 can include live hinges 1363 extending between portions or segments of the button 1365 in a direction parallel to a longitudinal axis of the outer sleeve 1362. In the illustrated embodiment, the button 1365 includes eight hinges 1363 separating the button 1365 into eight segments. However, the button 1365 can include more or fewer hinges 1363 separating the button 1365 into more or fewer segments. The hinges 1363 allow segments of the button 1365 to flex relative to each other. The button 1365 includes a lock tooth or protrusion 1366 extending from an inner wall of the button 1365 into the hollow interior of the button 1365. The lock tooth 1366 can be integrally formed with or attached to the inner wall of the button 1365. The inner rail 1364 includes a series of inner locking teeth 1368. The inner locking teeth 1368 are sized, shaped, and positioned to contact or engage with the lock tooth 1366. In other words, notches between adjacent inner locking teeth 1368 are configured to receive the lock tooth 1366.

In a neutral position or state, the lock tooth 1366 is disposed or seated in one of the notches between the inner locking teeth 1368, as shown in FIG. 29B. This restricts relative movement between the outer sleeve 1362 and inner rail 1364 and locks the adjustment mechanism and size of the headgear. The locking button 1365 and inner rail 1364 are sized such that, in the neutral state, the lock tooth 1366 is disposed at least partially in one of the notches between the inner locking teeth 1368 and there is a gap between sides of the inner rail 1364 and the inner wall of the locking button 1365. To adjust the length of the strap, the user squeezes the sides of the locking button 1365 as indicated by the arrows in FIG. 29B. Squeezing the sides of the locking button 1365 causes the lock tooth 1366 to lift out of the notch between the inner locking teeth 1368, as shown in FIG. 29C. When the sides of the locking button 1365 are squeezed to lift the lock tooth 1366 out of the notch, the sides of the inner wall of the locking button 1365 may contact the sides of the inner rail 1364, as shown in FIG. 29C. With the sides of the locking button 1365 squeezed and the lock tooth 1366 removed from the notch, the user can telescope the inner rail 1364 into or out of the outer sleeve 1362 to adjust the length of the strap. Once the user has achieved the desired strap length, he or she can release the squeeze on the locking button 1365 so that the outer sleeve 1362 returns to a neutral position and the lock tooth 1366 can be seated in another of the notches between inner locking teeth 1368 when the lock tooth 1366 and the notch are aligned.

In some embodiments, the inner locking teeth 1368 and lock tooth 1366 are angled or shaped to act as a ratchet in one direction and a lock in the other direction. In such an embodiment, the locking button 1365 allows for ratcheting movement in one direction (e.g., to shorten the strap and tighten the headgear) and resists or prevents movement in the opposite direction (e.g., to length the strap and loosen the headgear). The user can squeeze the sides of the locking button 1365 to release the lock and allow movement in the opposite direction.

FIGS. 30A-30H illustrate another example embodiment of an adjustment and/or locking mechanism that can be used with a headgear assembly. In some configurations, the adjustment and/or locking mechanism can be used with a headgear assembly such as the headgear assembly 2100. In the illustrated configuration, the headgear assembly includes an elastic sleeve 1372 that extends across the top of the user's head in use. The headgear assembly can also include an elastic sleeve 1373 that extends across the back of the user's head in use. One end of the elastic sleeve 1372 is coupled to a side junction 1374 that is positioned above one of the user's ear in use. In some configurations, the elastic sleeve 1372 extends between both side junctions 1374 and is sized to be as short as, or shorter than, the length of the top strap in a smallest size position. As such, the elastic sleeve acts to pull the two side junctions 1374 toward each other when the locking mechanism and any loads on the two side junctions 1374 are released. An end of the elastic sleeve 1373 can also be coupled to one or both of the side junctions 1374. A rail 1376 extends within the elastic sleeve 1372 and at least partially within the side junction 1374. The end of the rail 1376 positioned toward and/or within the side junction 1374 includes a series of rail teeth 1377 or the like. The opposite end of the rail 1376 can be functionally coupled to the elastic sleeve 1372 or can extend to the other side junction 1374 and include a series of rail teeth 1377 or the like. A lock tooth 1378 is moveably disposed within the side junction 1374. In the illustrated embodiment, an inner wall of the side junction 1374 that faces the rail teeth 1377 includes a recess 1375, and the lock tooth 1378 is moveably disposed within the recess 1375. A peak 1379 of the lock tooth 1378 is shaped to correspond to the rail teeth 1377. The headgear also includes a release trigger 1380 disposed within the side junction 1374.

In a default or resting position or state, the peak 1379 of the lock tooth 1378 engages the rail teeth 1377 as shown in FIG. 30B to lock or resist adjustment of the headgear. To adjust the headgear size, the user engages the release trigger 1380 to move the release trigger 1380 into engagement with the lock tooth 1378. This disengages the peak 1379 of the lock tooth 1378 from the rail teeth 1377, for example by forcing the lock tooth 1378 into the recess 1375 and away from the rail teeth 1377 as shown in FIG. 30C. In some configurations, the lock tooth 1378 is biased toward the rail teeth 1377 such that withdrawing the release trigger 1380 from the unlock position will result in the lock tooth 1378 moving toward the rail teeth 1377.

In some embodiments, the headgear is provided in an initial state with the elastic sleeve 1372 stretched to a maximum length, as shown in FIG. 30D. In this state, the peak 1379 of the lock tooth 1378 engages the rail teeth 1377 at or near the end of the rail 1376. To achieve the initial fit of the headgear, the user places the headgear on his or her head such that the side junction 1374 is positioned correctly above the user's ear. The user then engages the release trigger 1380 to disengage the lock tooth 1378 from the rail teeth 1377. The elastic sleeve 1372 then retracts toward its default length until the elastic sleeve 1372 is secure against the user's head. As the elastic sleeve 1372 retracts or shortens, the rail 1376 is forced farther into the side junction 1373. Once the elastic sleeve 1372 is secure against the user's head, the user can disengage the release trigger 1380 to allow the lock tooth 1378 to move back into engagement with the rail teeth 1377 and secure or lock the headgear in the correct size between (and inclusive of) a maximum elastic sleeve 1372 length shown in FIG. 30D and a minimum elastic sleeve 1372 length shown in FIG. 30E. This adjustment mechanism advantageously allows for a more automated initial fit adjustment process.

In some embodiments, the elastic strap 1373 can be adjusted similarly to the elastic strap 1372 (i.e., a second rail 1376 can extend within the elastic strap 1373 and the side junction 1374 can include a second lock tooth 1378 and/or release trigger 1380 to correspond to the second rail 1376).

To loosen the headgear while wearing it, the user can pull downward on the side junction 1374, for example from the position shown in FIG. 30F to the position shown in FIG. 30G, which forces the lock tooth 1378 to ratchet along the rail teeth 1377. Alternatively, the user can remove the headgear and pull the elastic sleeve 1372 and rail 1376 relative to the side junction 1374 (and/or pull the side junction 1374 relative to the elastic sleeve 1372 and rail 1376) to overcome the force between the lock tooth 1378 and rail teeth 1377 and/or ratchet the lock tooth 1378 and rail teeth 1377 relative to each other. As shown in FIG. 30H, in some embodiments, the rail teeth are angled to enhance the ratcheting function between the lock tooth 1378 and rail teeth 1377.

FIGS. 30I and 30J illustrate a variation of the adjustment mechanism of FIGS. 30A-30H in which the headgear includes two side junctions 1374, one positioned above each of the user's ears in use. Each end of the rail includes rail teeth, and each side junction 1374 includes a lock tooth and release trigger. A center of the elastic tube is joined to a center of the rail as shown. To adjust the headgear, the user activates the two release triggers to release the lock teeth from the rail teeth on both sides, and the elastic sleeve pushes the rail into the side junctions until the elastic sleeve is secure against the user's head. This variation advantageously allows for symmetrical adjustment of the headgear. Some configurations can be made in which only one side has the adjustment while the other side is fixed in position relative to the junction.

Whilst various adjustment arrangements and locking mechanisms have been described as being located within the top strap 2110, it is to be understood that in alternative embodiments the adjustment arrangements and locking mechanisms may be positioned in other locations within the headgear assembly. While various features have been described herein as part of, coupled to, or extending from one of the first and second straps 2112, 2114 of the headgear assembly 2100, such features can be reversed, for example, such that the features are part of, coupled to, or extend from the other of the first and second straps 2112, 2114.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to." Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavor in any country in the world.

Language of degree used herein, such as the terms "approximately," "about," "generally," and "substantially," as used herein represent a value, amount or characteristic close to the stated value, amount or characteristic that still performs a desired function or achieves a desired result. The deviation from the stated value, amount or characteristic could, for example, reflect acceptable tolerances, conversion factors, rounding off, measurement error, or other factors known to those of skill in the art. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A mask assembly comprising:
   a mask configured to contact a user's face and deliver gases to the user in use; and
   a headgear configured to secure the mask to the user's face in use, the headgear comprising:
      a top strap having a first strap and a second strap, wherein in use a portion of the first strap is configured to overlie a portion of the second strap such that an inner surface of the portion of the first strap faces an inner surface of the portion of the second strap; and
      an adjustment arrangement configured to connect and allow for adjustment between the first strap and the second strap, wherein the adjustment arrangement comprises a pair of outer rails protruding from the inner surface of the first strap and extending along a length of the first strap and a pair of inner rails protruding from the inner surface of the second strap and extending along a length of the second strap, wherein each of the length of the first strap and the length of the second strap are inelastic and bendable to allow curvature of the top strap;
      a lock fixed to one of the first and second straps, the lock configured to engage the other of the first and second straps to lock the first and second straps relative to each other,
      wherein the outer rails are configured to interlock with the inner rails such that friction between the outer rails and the inner rails allows the top strap to be slideably adjusted.

2. The mask assembly of claim 1, wherein the first and second straps are inelastic.

3. The mask assembly of claim 1, wherein the lock comprises a button pivotally attached to an end of the one of the first and second straps, the button comprising a retaining feature configured to engage the other of the first and second straps.

4. The mask assembly of claim 3, wherein the button is pivotally attached to the second strap, and the retaining feature comprises a post having a mushroom head, the mushroom head configured to engage with the outer rails of the first strap in a locked position.

5. The mask assembly of claim 1, wherein the lock comprises a button pivotally attached to an end of the second strap, the button comprising locking notches configured to engage teeth disposed on outer sides of the outer rails of the first strap in a locked position.

6. The mask assembly of claim 1, wherein the lock comprises a cantilevered arm.

7. The mask assembly of claim 6, wherein the cantilevered arm is configured to engage notches between the inner or outer rails of the other of the first and second straps.

8. The mask assembly of claim 7, further comprising a pull tab coupled to the cantilevered arm, the pull tab configured to be pulled to disengage the cantilevered arm from the notches.

9. The mask assembly of claim 8, wherein the pull tab is elastic.

10. The mask assembly of claim 1, wherein the lock comprises a flexible tooth and a slide lock, the flexible tooth is configured to engage notches on the other of the first and second straps, when the slide lock is in a first position the slide lock holds the flexible tooth in engagement with the notches, and when the slide lock is in a second position the flexible tooth disengages from the notches.

11. The mask assembly of claim 1, wherein the lock comprises a gear, an end of one of the first and second straps comprises a flexible tooth, the other of the first and second straps comprises a gear profile corresponding to teeth of the gear, and the gear interacts with the flexible tooth and the gear profile.

12. The mask assembly of claim 1, wherein the portion of the first strap and the portion of the second strap cooperate to define an overlapping portion of the top strap having a length that is variable by the adjustment arrangement, wherein the inner rails and the outer rails are interlocked within an entirety of the overlapping portion of the top strap in all adjustment positions.

13. A headgear for a respiratory mask having an adjustment arrangement comprising a first elongated strap that is a first member of the headgear; a second elongated strap that is a second member of the headgear that are overlapping within an overlapping portion of the adjustment arrangement and slideably engaged, by a pair of interlocking rails; a lock fixed to one of the first and second straps, the lock configured to secure the first and second straps in a user defined position, wherein the first elongated strap and the second elongated strap are inelastic and bendable within an entirety of the overlapping portion.

14. The headgear of claim 13, wherein the pair of rails include a pair of inner rails and a pair of outer rails.

15. The headgear of claim 13, wherein each of the rails includes a flange, configured to secure the straps together.

16. The headgear of claim 13, wherein the interlocking rails are interlocked within an entirety of the overlapping portion of the top strap in all adjustment positions.

* * * * *